United States Patent
Benner et al.

(10) Patent No.: US 11,458,146 B2
(45) Date of Patent: *Oct. 4, 2022

(54) COMPOSITIONS AND METHODS FOR THE TREATMENT OF MYELIN RELATED AND INFLAMMATION RELATED DISEASES OR DISORDERS

(71) Applicant: Duke University, Durham, NC (US)

(72) Inventors: Eric Benner, Durham, NC (US); Simon Gregory, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/477,826

(22) PCT Filed: Jan. 12, 2018

(86) PCT No.: PCT/US2018/013525
§ 371 (c)(1),
(2) Date: Jul. 12, 2019

(87) PCT Pub. No.: WO2018/132676
PCT Pub. Date: Jul. 19, 2018

(65) Prior Publication Data
US 2019/0336512 A1 Nov. 7, 2019

Related U.S. Application Data

(60) Provisional application No. 62/446,211, filed on Jan. 13, 2017.

(51) Int. Cl.
*A61K 31/575* (2006.01)
*A61P 1/04* (2006.01)
*A61K 45/06* (2006.01)

(52) U.S. Cl.
CPC ............ *A61K 31/575* (2013.01); *A61K 45/06* (2013.01); *A61P 1/04* (2018.01)

(58) Field of Classification Search
CPC ......... A61K 31/575; A61K 45/06; A61P 1/04; A61P 29/00
See application file for complete search history.

(56) References Cited

U.S. PATENT DOCUMENTS

| | | | |
|---|---|---|---|
| 4,743,597 A | 5/1988 | Javitt et al. | |
| 5,310,742 A * | 5/1994 | Elias | A61K 31/415 514/274 |
| RE37,999 E | 2/2003 | Tipton et al. | |
| 7,339,065 B2 | 3/2008 | Avery et al. | |
| 8,165,819 B2 * | 4/2012 | Clermont | G16H 50/50 702/19 |
| 8,604,011 B2 | 12/2013 | Mellon | |
| 9,532,968 B1 * | 1/2017 | Nguyen | C07D 295/185 |
| 9,746,481 B2 | 8/2017 | Everett et al. | |
| 10,238,664 B2 | 3/2019 | Benner | |
| 2002/0010128 A1 | 1/2002 | Parks et al. | |
| 2005/0019765 A1 | 1/2005 | Wellington et al. | |
| 2006/0009433 A1 | 1/2006 | Yao et al. | |
| 2006/0035873 A1 | 2/2006 | Niesor et al. | |
| 2007/0093470 A1 | 4/2007 | Chao et al. | |
| 2010/0286053 A1 | 11/2010 | Kuan et al. | |
| 2014/0179656 A1 | 6/2014 | Kuang et al. | |
| 2014/0308687 A1 | 10/2014 | Keller et al. | |
| 2017/0007739 A1 | 1/2017 | Reves et al. | |
| 2017/0196892 A1 | 7/2017 | Benner | |

FOREIGN PATENT DOCUMENTS

| | | |
|---|---|---|
| WO | WO 2002/011708 A2 | 2/2002 |
| WO | WO 2008/071960 A2 | 6/2008 |
| WO | 2011/103175 A2 | 8/2011 |
| WO | WO 2013/040441 A1 | 3/2013 |
| WO | 2013/154752 A1 | 10/2013 |
| WO | WO 2016/007762 A1 | 1/2016 |
| WO | WO 2016/172658 A2 | 10/2016 |
| WO | 2017/007836 A1 | 1/2017 |
| WO | WO 2018/132676 A1 | 7/2018 |

OTHER PUBLICATIONS

Alberta, "Sonic Hedgehog is Required during an Early Phase of Oligodendrocyte Development in Mammalian Brain," Molecular and Cellular Neuroscience, 2001, 18, 434-441.
Ayciriex et al., "Development of a novel method for quantification of sterols and oxysterols by UPLC-ESI-HRMS: application to a neuroinflammation rat model," Anal Bioanal Chem, 2012, 404, 3049-3059.
Back et al., "Maturation-Dependent Vulnerability of Perinatal White Matter in Premature Birth," Stroke, 2007, 38, 724-730.
Bai et al., "Gli1 can rescue the in vivo function of Gli2," Development, 2001, 128, 5161-5172.
Beaino et al., "Predictors of cerebral palsy in very preterm infants: the EPIPAGE prospective population-based cohort study," Dev Med Child Neurol, 2010, 52, e119-25.
Benner et al., "Protective astrogenesis from the SVZ niche after injury is controlled by Notch modulator Thbs4," Nature, 2013, 497, 369-373.
Bigler et al., "Volumetric and Voxel-Based Morphometry Findings in Autism Subjects With and Without Macrocephaly," Dev Neuropsychol, 2010, 35(3): 278-295.
Billiards et al., "Myelin abnormalities without oligodendrocyte loss in periventricular leukomalacia," Brain Pathol, 2008, 18, 153-163.
Bittner et al., "Myelin oligodendrocyte glycoprotein (MOG35-55) induced experimental autoimmune encephalomyelitis (EAE) in C57BL/6 mice," J. Vis. Exp., 2014, 86: 51275, 5 pages.

(Continued)

*Primary Examiner* — Barbara P Badio
(74) *Attorney, Agent, or Firm* — Polsinelli PC

(57) ABSTRACT

Described are oxysterols, pharmaceutical compositions including the oxysterols, and methods of using the oxysterols and compositions for treating diseases and/or disorders related to inflammation, such as necrotizing enterocolitis, mesenteric ischemia, inflammatory bowel diseases including Crohn's disease and ulcerative colitis, lymphocytic colitis, Celiac disease. Behcet's disease, rheumatoid arthritis, psoriasis, and autoimmune thyroid disease.

14 Claims, 17 Drawing Sheets

(56) References Cited

OTHER PUBLICATIONS

Björkhem et al., "Brain Cholesterol: Long Secret Life Behind a Barrier," Arterioclerosis, Thrombosis and Vascular Biology, 2004, 24(5):806-815.
Björkhem et al., "Oxysterols—Friends, Foes, or Just Fellow Passengers?," Arterioscler Thromb Vasc Biol, 2002, 22:734-742.
Briscoe et al., "The mechanisms of Hedgehog signalling and its roles in development and disease," Nature Publishing Group, 2013, 14, 416-429.
Buser et al., "Arrested preoligodendrocyte maturation contributes to myelination failure in premature infants," Ann Neurol, 2012, 71, 93-109.
C.T.F.A., Cosmetic Ingredient Handbook, 1992, pp. 587-592.
Cao et al., "Transplantation of ciliary neurotrophic factor-expressing adult oligodendrocyte precursor cells promotes remyelination and functional recovery after spinal cord injury," Journal of Neuroscience, 2010, vol. 30, Issue 8, pp. 2989-3001.
Caporaso et al., "Ultra-high-throughput microbial community analysis on the Illumina HiSeq and MiSeq platforms," ISME J, 2012, 6, 1621-1624.
Cartagena et al., "24S-hydroxycholesterol effects on lipid metabolism genes are modeled in traumatic brain injury," 2010, Brain Research, vol. 1319, pp. 1-12. (Year: 2010).
Centers for Disease Control and Prevention (CDC), "Economic costs associated with mental retardation, cerebral palsy, hearing loss, and vision impairment—United States, 2003," MMWR Morb Mortal Wkly Rep, 2004, 53, 57-59.
Chau et al., "Postnatal infection is associated with widespread abnormalities of brain development in premature newborns," Pediatr Res, 2012, 71, 274-279.
Cochary et al., "Presence of the plasma membrane proteolipid (plasmolipin) in myelin," J. Neurochem, 1990, 55, 602-610.
Colver et al., "Cerebral palsy," The Lancet, 2014, 383, 1240-1249.
Corcoran et al., "Oxysterols stimulate Sonic hedgehog signal transduction and proliferation of medulloblastoma cells," Proc Natl Acad Sci USA, 2006, 103, 8408-8413.
Cortez et al., "Maternal milk feedings reduce sepsis, necrotizing enterocolitis and improve outcomes of premature infants," J Perinatol, 2018, 38, 71-74.
Counsell et al., "Diffusion-weighted imaging of the brain in preterm infants with focal and diffuse white matter abnormality," PEDIATRICS, 2003, 112, 1-7.
Deng et al., "Direct visualization of membrane architecture of myelinating cells in transgenic mice expressing membrane-anchored EGFP," Genesis, 2014, 52, 341-349.
Deoni et al., "Breastfeeding and early white matter development: A cross-sectional study," NeuroImage, 2013, 82, 77-86.
Deoni et al., "White-matter relaxation time and myelin water fraction differences in young adults with autism," Psychological Medicine, 2015, 45, 795-805.
Du et al., "Myelin and Axon Abnormalities in Schizophrenia Measured with Magnetic Resonance Imaging Techniques," Biological Psychiatry, 2013, 74(6), 451-457.
Dwyer et al., "Oxysterols are novel activators of the hedgehog signaling pathway in pluripotent mesenchymal cells," Journal of Biological Chemistry, 2007, 282, 8959-8968.
Egan et al., "Toll-like receptor 4-mediated lymphocyte influx induces neonatal necrotizing enterocolitis," J. Clin. Invest., 2016, 126, 495-508.
Fard et al., "BCAS1 expression defines a population of early myelinating oligodendrocytes in multiple sclerosis lesions," Sci Transl Med, 2017, 9, eaam7816.
Ferent et al., "Sonic Hedgehog signaling is a positive oligodendrocyte regulator during demyelination," J. Neurosci, 2013, 33, 1759-1772.
Fischer et al., "Expression of plasmolipin in oligodendrocytes," J. Neurosci. Res, 1991, 28, 81-89.
Gabbi, C., Warner, M. & Gustafsson, J.-Å. Biochemical and Biophysical Research Communications. Biochemical and Biophysical Research Communications, 2014, 647-650.

Gibertoni et al., "Positive Effect of Human Milk Feeding during NICU Hospitalization on 24 Month Neurodevelopment of Very Low Birth Weight Infants: An Italian Cohort Study," PLoS ONE, 2015, 10, e0116552, 13 pages.
Gill et al., "Sterol regulators of cholesterol homeostasis and beyond: The oxysterol hypothesis revisited and revised," Progress in Lipid Research, 2008, 47(6), pp. 391-404.
Hack et al., "Chronic conditions, functional limitations, and special health care needs of school-aged children born with extremely low-birth-weight in the 1990s," JAMA, 2005, 294, 318-325.
Hermann et al., "Brain development in children with new onset epilepsy: A prospective controlled cohort investigation," Epilepsia, 2010, 51(10), 2038-2046.
Im-Emsap et al., "Disperse Systems," Modern Pharmaceutics, 1979, Chapter 9.
Iupac, "Rules for the Nomenclature of Organic Chemistry, Section E: Stereochemistry, Recommendations 1974," Pure & Appl. Chem., 1976, vol. 45, pp. 11-30.
Janowski et al., "An oxysterol signalling pathway mediated by the nuclear receptor LXR alpha," Nature, 1996, 383, 728-731.
Kase et al., "22-Hydroxycholesterols regulate lipid metabolism differently than T0901317 in human myotubes," Biochim Biophys Acta, 2006, 1761, 1515-1522.
Kim et al., "20(S)-Hydroxycholesterol Inhibits PPARγ Expression and Adipogenic Differentiation of Bone Marrow Stromal Cells Through a Hedgehog-Dependent Mechanism," Journal of Bone and Mineral Research, 2007, 22, 1711-1719.
Klevay, "Myelin and traumatic brain injury: The copper deficiency hypothesis," Medical Hypotheses 2013, 81(6), 995-998.
Kottke et al., "Tablet Dosage Forms," Modern Pharmaceutics, 1979, Chapter 10.
Kuczynski et al., "Using QIIME to analyze 16S rRNA gene sequences from microbial communities," Curr Protoc Microbiol, 2012, Chapter 1, Unit 10.7, 28 pages.
Lagace et al., "Dynamic contribution of nestin-expressing stem cells to adult neurogenesis," Journal of Neuroscience, 2007, 27, 12623-12629.
Lauth et al., "Inhibition of GLI-mediated transcription and tumor cell growth by small-molecule antagonists," Proc Natl Acad Sci USA, 2007, 104, 8455-8460.
Le Mandat Schultz et al., "Expression of TLR-2, TLR-4, NOD2 and pNF-κB in a Neonatal Rat Model of Necrotizing Enterocolitis," PLoS ONE, 2007, 2, e1102-9.
Lehmann et al., "Activation of the nuclear receptor LXR by oxysterols defines a new hormone response pathway," Journal of Biological Chemistry, 1997, 272, 3137-3140.
Leoni et al., "Side chain oxidized oxysterols in cerebrospinal fluid and the integrity of blood-brain and blood-cerebrospinal fluid barriers," Journal of Lipid Research, 2003, 44(4): 793-799.
Lin et al., "The detection of 20(S)—hydroxycholesterol in extracts of rat brains and human placenta by a gas chromatograph/mass spectrometry technique," The Journal of Steroid Biochemistry and Molecular Biology, 2003, 85, 57-61.
Madan et al., "Gut microbial colonisation in premature neonates predicts neonatal sepsis," Archives of Disease in Childhood—Fetal and Neonatal Edition, 2012, 97, F456-62.
Mai et al., "Distortions in development of intestinal microbiota associated with late onset sepsis in preterm infants," PLoS ONE, 2013, 8, e52876.
Makoukji et al., "Interplay between LXR and Wnt/β—Catenin Signaling in the Negative Regulation of Peripheral Myelin Genes by Oxysterols," The Journal of Neuroscience, 2011, 31(26): 9620-9629.
Martinez-Biarge et al., "Predicting motor outcome and death in term hypoxic-ischemic encephalopathy," Neurology, 2011, 76, 2055-2061.
Maxwell, "Damage to Myelin and Oligodendrocytes: A Role in Chronic Outcomes Following Traumatic Brain Injury?," Brain Sci, 2013, 3(3): 1374-1394.
McCutcheon's vol. 1, Emulsifiers & Detergents, 1994, North American Edition, pp. 236-239.

(56) References Cited

OTHER PUBLICATIONS

McIntyre et al., "A systematic review of risk factors for cerebral palsy in children born at term in developed countries," Dev Med Child Neurol, 2013, 55, 499-508.
McMurdie et al., "phyloseq: an R package for reproducible interactive analysis and graphics of microbiome census data," PLoS ONE, 2013, 8, e61217.
Meffre et al., "Liver X receptors alpha and beta promote myelination and remyelination in the cerebellum," Proceedings of the National Academy of Sciences of the United States of America, 2015, vol. 112, No. 24, pp. 7592.
Meffre et al., "Opposite effect of LXR on myelination process in the central and peripheral nervous systems and interplay with Wnt pathways," Endocrine Abstracts, 2012. Retreived from the Internet on Dec. 14, 2017 <http://www.endocrine-abstracts.org/ea/0029/ea0029p487.htm>.
Mercier et al., "Ne urodevelop mental outcome of extremely low birth weight infants from the Vermont Oxford network: 1998-2003," Neonatology, 2010, 97, 329-338.
Miller et al., "Experimental autoimmune encephalomyelitis in the mouse," Curr Protoc Immunol, 2007, Unit-15.1, 26 pages.
Mitha et al., "Neonatal Infection and 5-year Neurodevelopmental Outcome of Very Preterm Infants," Pediatrics, 2013, 132, e372-e380.
Nachtergaele et al., "Oxysterols are allosteric activators of the oncoprotein Smoothened," Nature Chemical Biology, 2012, 8, 211-220.
Nedelcu et al., "Oxysterol binding to the extracellular domain of smoothened in Hedgehog signaling," Nature Chemical Biology, 2013, 9, 557-564.
Nobuta et al., "STAT3—mediated astrogliosis protects myelin development in neonatal brain injury," Ann Neurol. 2012, 72(5): 750-765.
Ortega et al., "Sonic hedgehog promotes generation and maintenance of human forebrain Olig2 progenitors," Front Cell Neurosci, 2013, 7, 254.
Pandit et al., "Diffusion magnetic resonance imaging in preterm brain injury," Neuroradiology, 2013, 55, 65-95.
Paredes et al., "Extensive migration of young neurons into the infant human frontal lobe," Science, 2016, 354(6308): aaf7073, 14 pages.
Pataj et al., "Quantification of oxysterols in human plasma and red blood cells by liquid chromatography high-resolution tandem mass spectrometry," Journal of Chromatography A, 2016, 1439, 82-88.
Paulson et al., "Differential abundance analysis for microbial marker-gene surveys," Nat Methods, 2013, 10, 1200-1202.
Przygonski et al., "Determination of cholesterol oxidation products in milk powder and infant formulas by gas chromatography and mass spectrometry," Nahrung, 2000, 44, 122-125.
Ragot et al., "Absence of correlation between oxysterol accumulation in lipid raft microdomains, calcium increase, and apoptosis induction on 158N murine oligodendrocytes," Biochemical Pharmacology, 2013, 86, 67-79.
Remington's Pharmaceutical Sciences, 15th Ed. 1975, pp. 335-337.
Rohatgi et al., "Patched1 Regulates Hedgehog Signaling at the Primary Cilium," Science, 2007, 317, 372-376.
Samanta et al., "Inhibition of Gli1 mobilizes endogenous neural stem cells for remyelination," Nature, 2015, 526(7373): 448-452.
Shah et al., "Adverse Neurodevelopment in Preterm Infants with Postnatal Sepsis or Necrotizing Enterocolitis is Mediated by White Matter Abnormalities on Magnetic Resonance Imaging at Term," The Journal of Pediatrics, 2008, 153, 170-175.e1.
Shankaran et al., "Whole-Body Hypothermia for Neonates with Hypoxic-Ischemic Encephalopathy," N Engl J Med 2005, 353: 1574-1584.
Sorrells et al., "Human hippocampal neurogenesis drops sharply in children to undetectable levels in adults," Nature, 2018, 555, 377-381.
Svensson et al., "Crystal structure of the heterodimeric complex of LXRα and RXRβ ligand-binding domains in a fully agonistic conformation," EMBO J, 2003, 22, 4625-4633.
Volpe et al., "The developing oligodendrocyte: key cellular target in brain injury in the premature infant," International Journal of Developmental Neuroscience: the Official Journal of the International Society for Developmental Neuroscience, 2011, 29, 423-440.
Volpe, "Brain injury in premature infants: a complex amalgam of destructive and developmental disturbances," The Lancet Neurology, 2009, 8(1): 110-124.
Volpe, "Postnatal Sepsis, Necrotizing Enterocolitis, and the Critical Role of Systemic Inflammation in White Matter Injury in Premature Infants," The Journal of Pediatrics, 2008, 153(2): 160-163.
Wang, "Role of Sonic Hedgehog Signaling in Oligodendrocyte Differentiation," Neurochem Res, 2016, 41, 3289-3299.
Weiner et al., "Plasma 24S-hydroxycholesterol and other oxysterols in acute closed head injury," Brain Inj, 2008, 22(7-8): 611-615.
Woodward et al., "Neonatal MRI to predict ne urodevelopmental outcomes in preterm infants," N Engl J Med, 2006, 355, 685-694.
Woodward et al., "Neonatal White Matter Abnormalities an Important Predictor of Neurocognitive Outcome for Very Preterm Children," PLoS ONE, 2012, 7, e51879, 9 pages.
Wynn et al., "Defective innate immunity predisposes murine neonates to poor sepsis outcome but is reversed by TLR agonists," Blood, 2008, 112, 1750-1758.
Wynn et al., "Increased mortality and altered immunity in neonatal sepsis produced by generalized peritonitis," Shock, 2007, 28(6): 675-683.
You et al., "Myelin damage of hippocampus and cerebral cortex in rat pentylenetetrazol model," Brain Research, 2011, 1381, 208-216.
Zhou et al., "Longitudinal analysis of the premature infant intestinal microbiome prior to necrotizing enterocolitis: a case-control study," PLoS ONE, 2015, 10, e0118632.
Zuercher et al., "Discovery of tertiary sulfonamides as potent liver X receptor antagonists," J Med Chem, 2010, 53, 3412-3416.
International Search Report and Written Opinion for Application No. PCT/US2015/039770 dated Oct. 8, 2015 (9 pages).
International Search Report and Written Opinion for Application No. PCT/US2018/013525 dated Apr. 4, 2018 (11 pages).
United States Patent Office Action for U.S. Appl. No. 15/325,039 dated Dec. 21, 2017 (11 pages).
United States Patent Office Notice of Allowance for U.S. Appl. No. 15/325,039 dated Nov. 1, 2018 (5 pages).
United States Patent Office Action for U.S. Appl. No. 16/265,438 dated Jan. 24, 2020 (14 pages).
Frohman et al., "Multiple Sclerosis—The Plaque and Its Pathogenesis," The New England Journal of Medicine, 2006, 354(9):942-955.
European Patent Office Extended Search Report for Application No. 18738460.7 dated Aug. 4, 2020 (11 pages).
Communication Pursuant to Article 94(3) EPC for European Application No. 15818122.1 dated Jan. 7, 2020 (Applicant—Duke University) (5 pages).
Communication Conveying Extended European Search Report for European Application No. 15818122.1 dated Jan. 19, 2018 (Applicant—Duke University) (9 pages).
Poli G, et al. (2013) Oxysterols in the pathogenesis of major chronic diseases. Redox Biol. 1(1):125-130.
Notice of Allowance dated Apr. 8, 2022 for U.S. Appl. No. 16/910,706, filed Jun. 24, 2020(Applicant—Duke University) (5 pages).

* cited by examiner

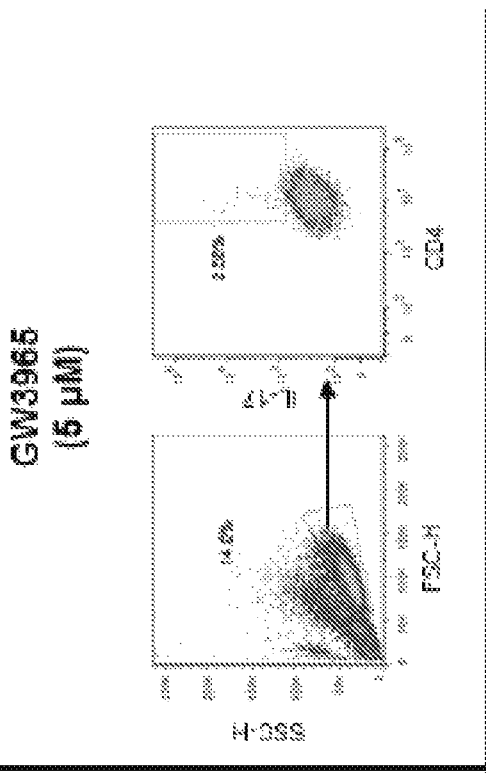
FIG. 8A
FIG. 8B
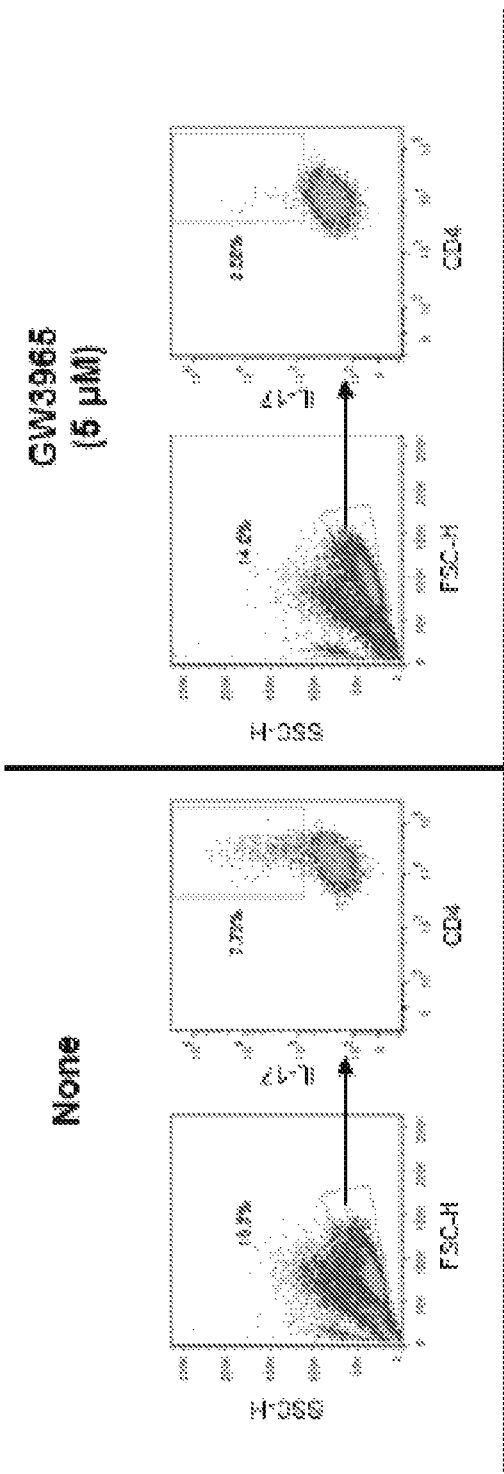
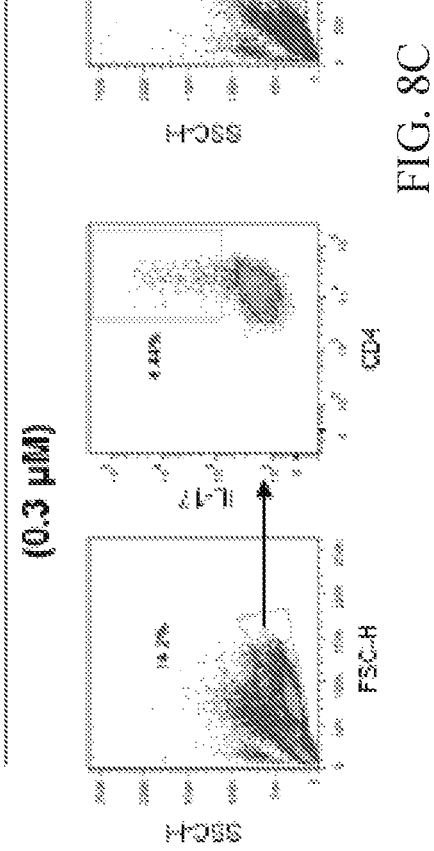
FIG. 8C

COMPOSITIONS AND METHODS FOR THE TREATMENT OF MYELIN RELATED AND INFLAMMATION RELATED DISEASES OR DISORDERS

CROSS-REFERENCE TO RELATED APPLICATIONS

This patent application is the U.S. national stage entry, under 35 U.S.C. § 371, of International Application Number PCT/US2018/013525, filed Jan. 12, 2018, which claims the benefit of U.S. Provisional Patent Application No. 62/446,211, filed Jan. 13, 2017, the entire contents of which are hereby incorporated by reference.

TECHNICAL FIELD

The present disclosure relates to compounds, compositions, and methods for treating diseases and/or disorders related to myelin injury, such as neonatal brain injury, traumatic brain injury, spinal cord injury, cerebral palsy, seizures, cognitive delay, multiple sclerosis, stroke, autism, leukodystrophy, schizophrenia and bipolar disorder. The present disclosure also relates to compounds, compositions, and methods for treating diseases and/or disorders related to inflammation, such as necrotizing enterocolitis, mesenteric ischemia, inflammatory bowel diseases such as Crohn's disease and ulcerative colitis, lymphocytic colitis, Celiac disease, Behcet's disease, rheumatoid arthritis, psoriasis, and autoimmune thyroid disease.

BACKGROUND

About 10% of infants in the United States are born premature and are at significant risk for brain injuries, which may lead to disorders such as cerebral palsy, seizures, and cognitive delay. Myelin injury is the most common form of brain injury impacting neurodevelopment in premature infants. Currently there are no effective therapies for myelin injuries.

Premature infants are also at a significant risk for necrotizing enterocolitis, which is characterized by bowel wall injury and/or necrosis, inflammation of the bowel, and subsequent invasion of the bowel wall with gut microbes, which leads to sepsis. Necrotizing enterocolitis is the most common cause of surgical emergencies within this population.

Accordingly, there exists a need for effective therapies for brain injuries resulting from damaged myelin, and inflammatory diseases such as necrotizing enterocolitis in premature infants.

SUMMARY OF THE INVENTION

In one aspect, disclosed is a method of treating diseases or disorders related to inflammation in a subject in need thereof, the method comprising administering a therapeutically effective amount of at least one oxysterol.

Also disclosed are pharmaceutical compositions comprising an oxysterol, and methods of using the pharmaceutical compositions for treatment of diseases and/or disorders related to inflammation.

BRIEF DESCRIPTION OF THE SEVERAL VIEWS OF THE DRAWING(S)

Figure 5:
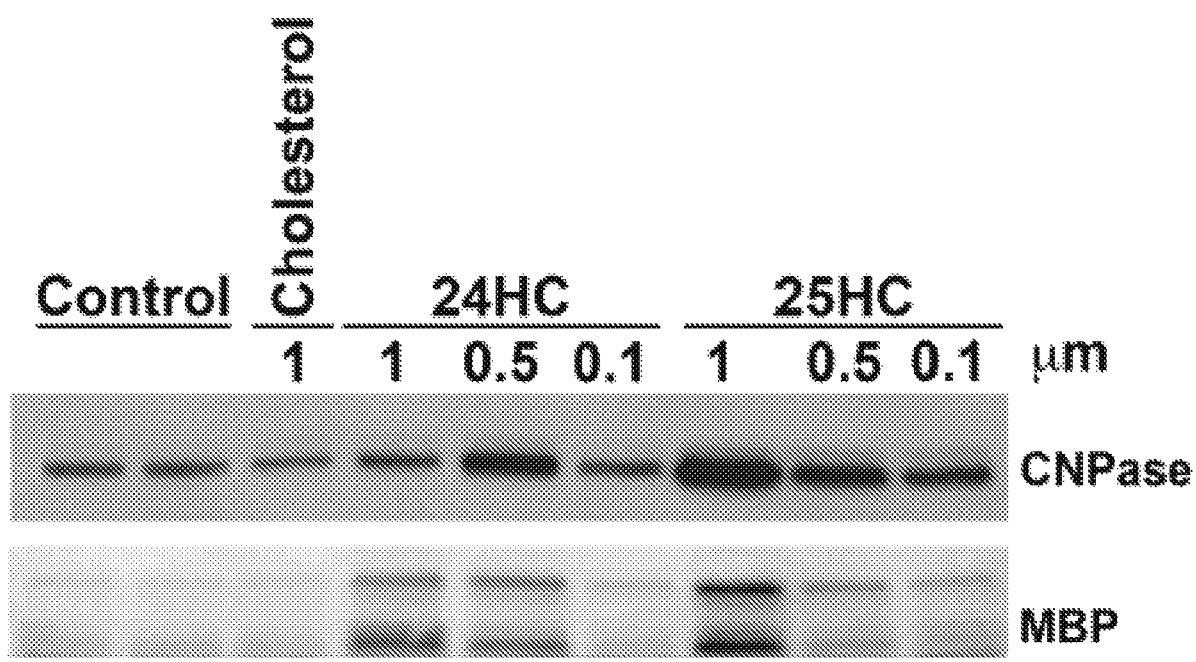

FIG. 5 is a western blot analysis. Stem cells were treated with oxysterols at doses indicated for 5 days then allowed to differentiate for 18 days. Protein lysates were probed for oligodendrocyte-associated proteins CNPase and myelin basic protein (MBP).

Figure 6A:
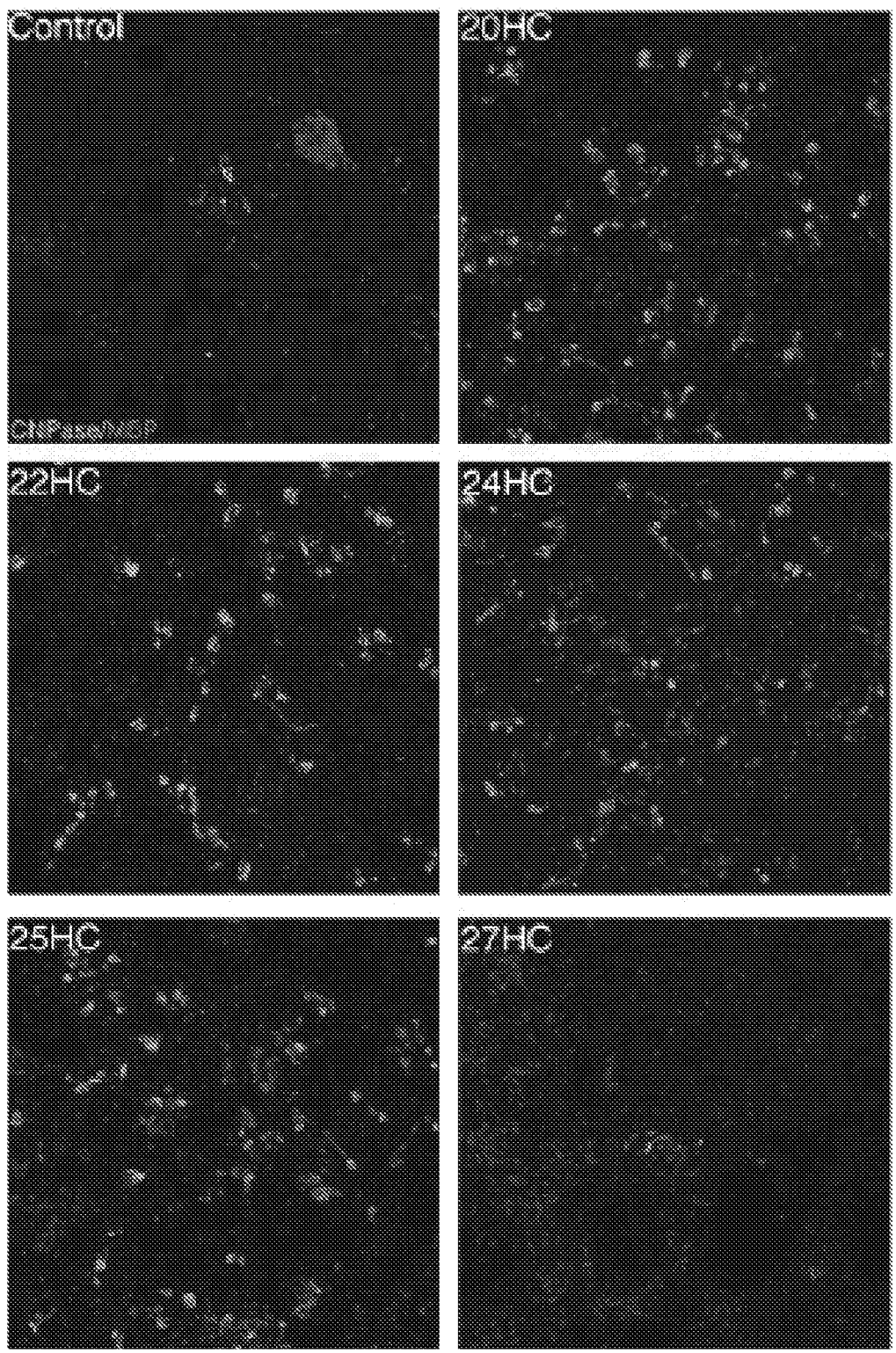

FIG. 6A is a series of confocal micrographs showing differentiated stem cells that were stained for CNPase (green) and myelin basic protein (MBP, red).

Figure 6B:
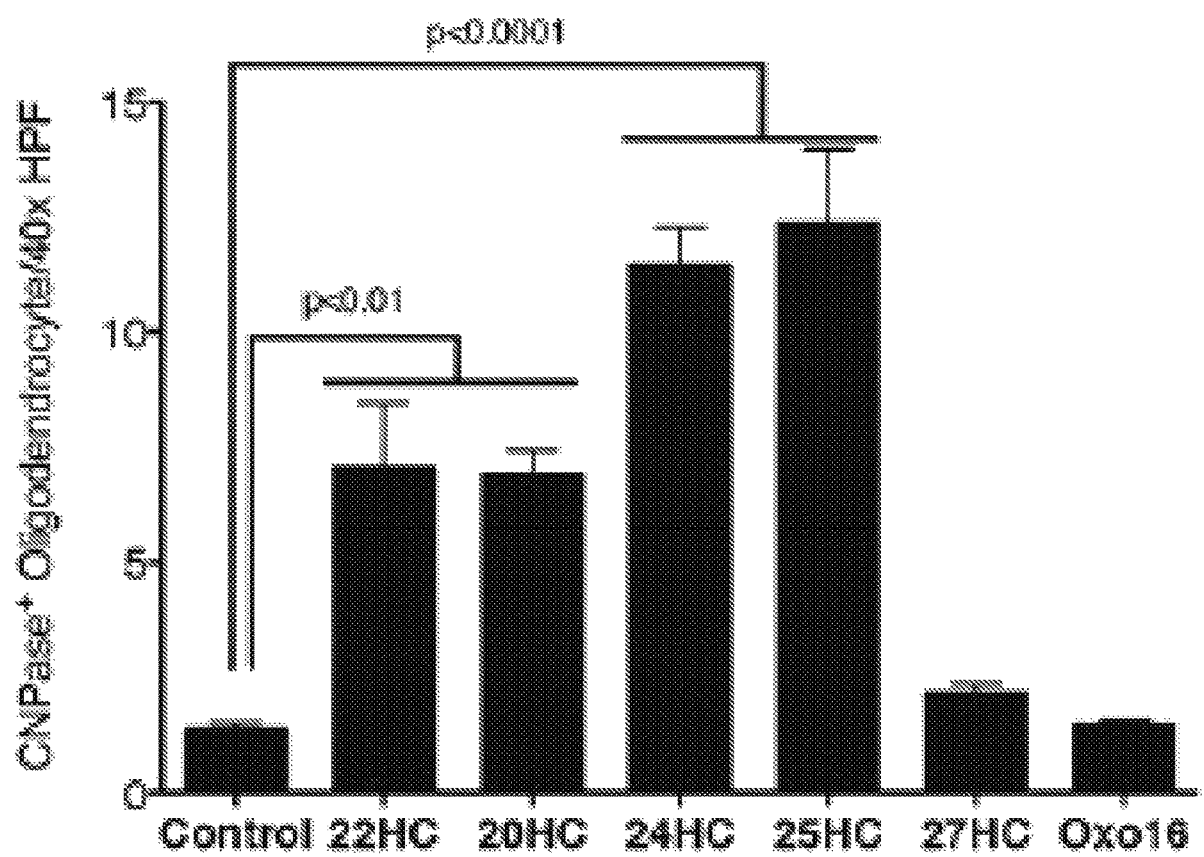

FIG. 6B is a quantification of the number of CNPase+ oligodendrocytes from computer selected 40× fields.

Figure 7:
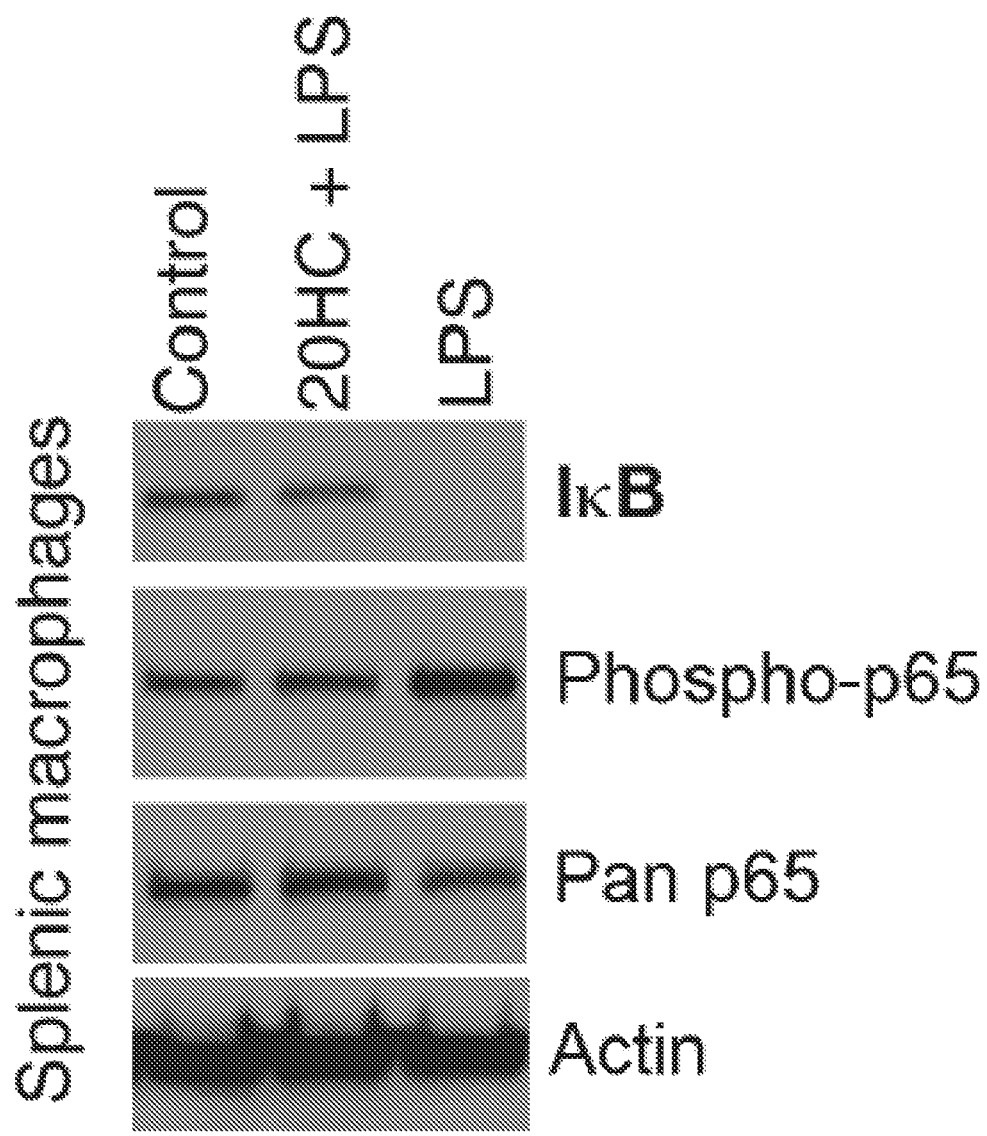
Figures 8D, 8E:
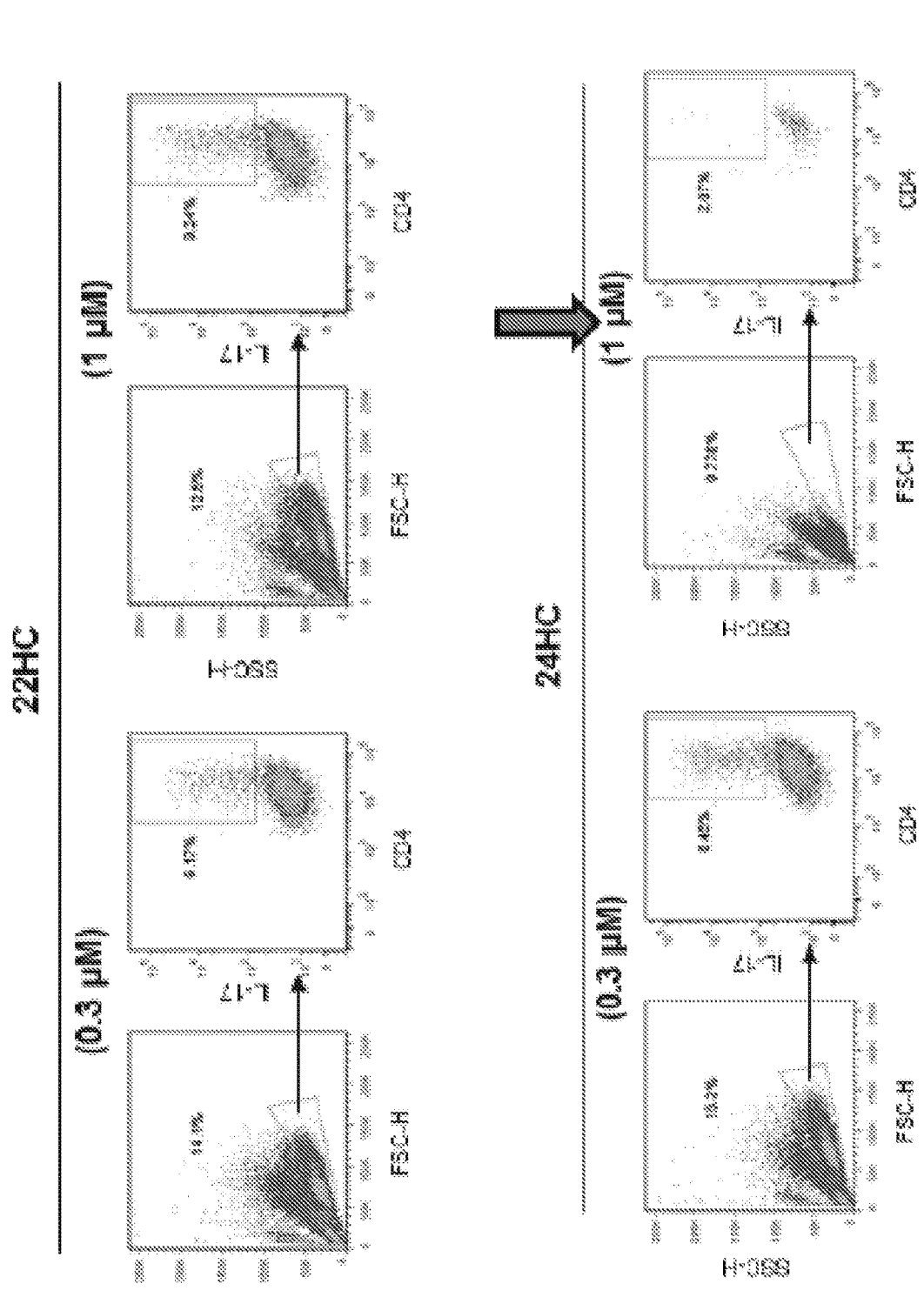
Figure 8F:
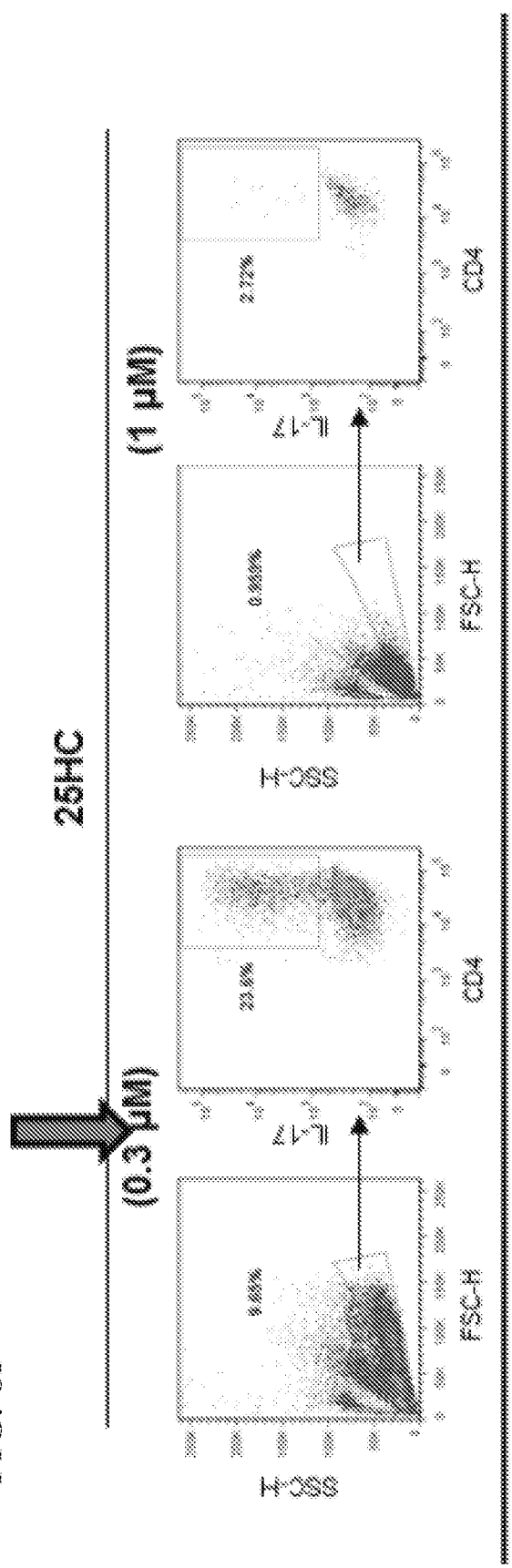
Figure 8G:
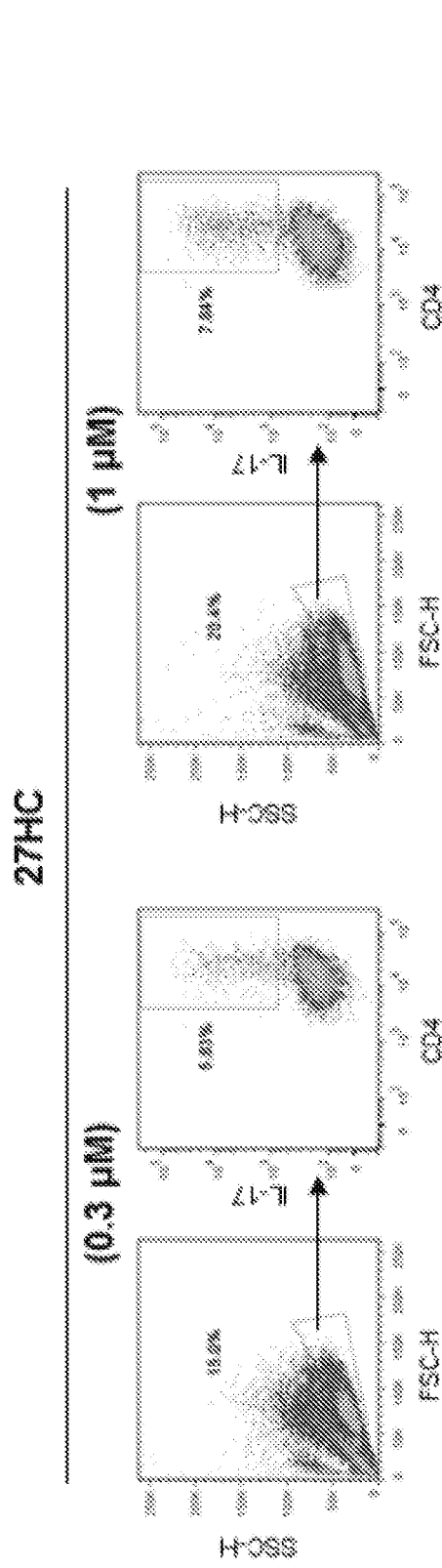

FIG. 7 is a Western blot showing the 20HC inhibition of NFκB pathway in primary splenic monocytes. Primary monocytes were exposed to media, 20HC (24 hour)+LPS (500 ng/ml), or LPS alone for 4 hours. 20HC prevented IκB degradation and p65 phosphorylation in LPS treated cells.

FIGS. 8A-G are graphs of flow cytometry analysis of the effect of oxysterols on the augmentation of TH17. 20HC (C) and 24HC (E) decrease TH17 polarization. Low doses of 25HC (F) promote TH17 polarization.

Figure 9A:
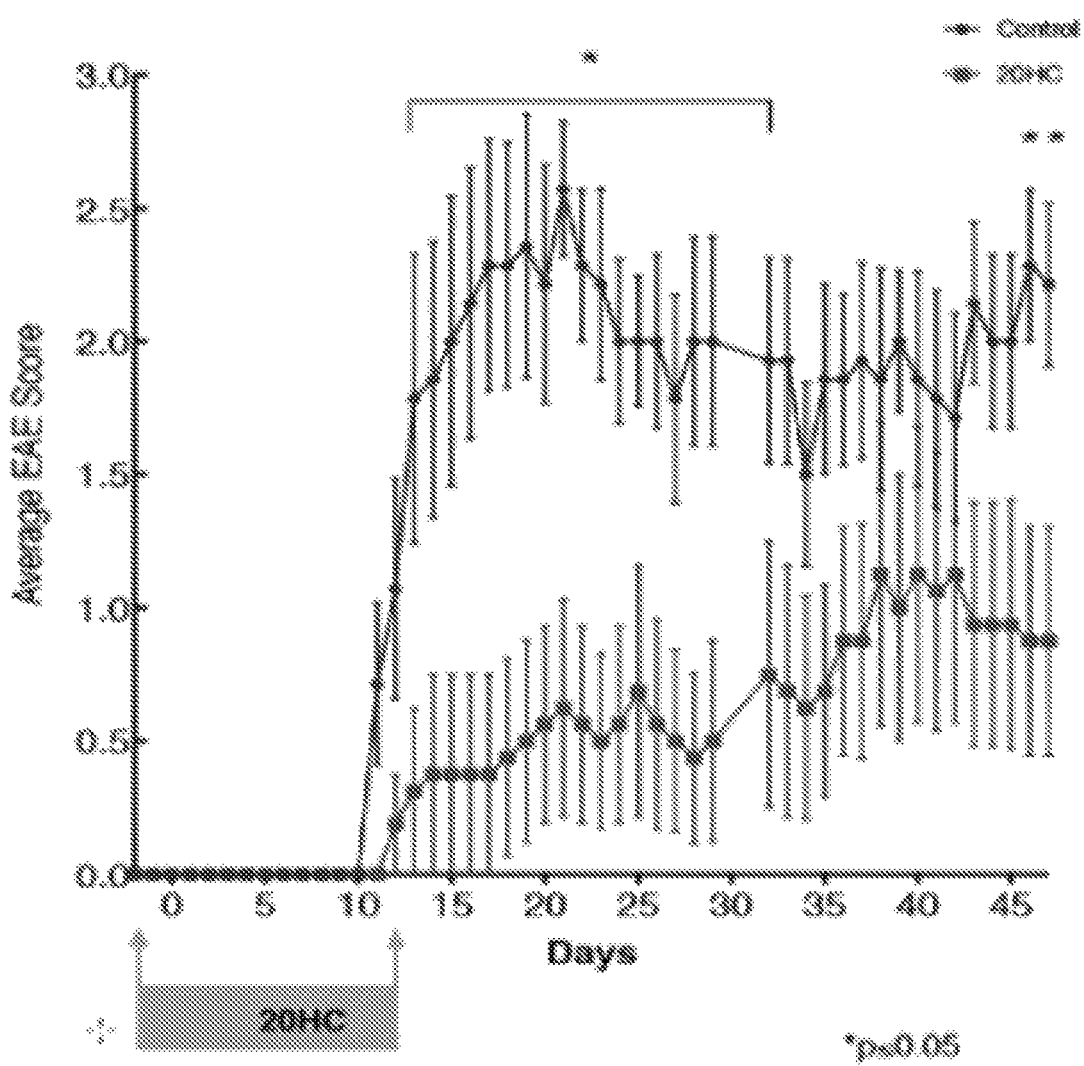
Figure 9B:
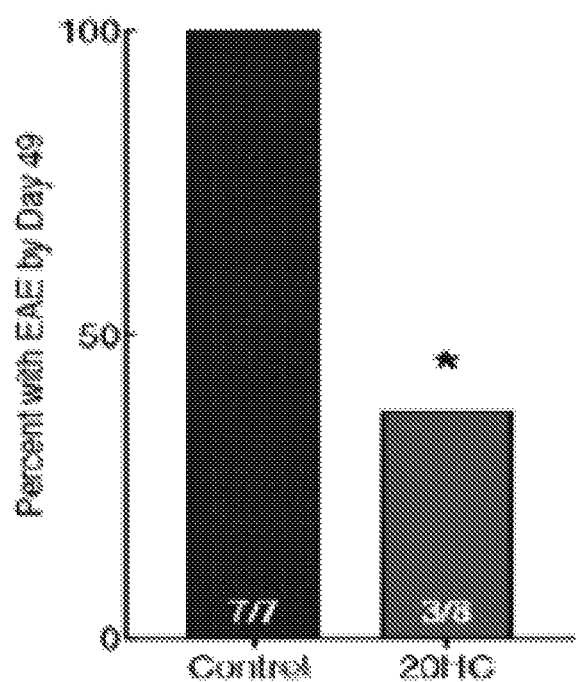

FIG. 9A is a graph illustrating attenuation of EAE clinical score in 20HC-treated mice (bottom squared line) compared to control mice (top dotted line) over a period of 46 days; dots on 20HC treatment group indicate days at which three 20HC-treated mice displayed symptoms. FIG. 9B is a graph which shows the number of mice in the control and 20HC treatment groups that developed EAE. Significance was determined using individual t testing each day (FIG. 9A, p≤0.05) or Fisher exact test (FIG. 9B).

DETAILED DESCRIPTION OF THE INVENTION

Disclosed herein are oxysterols useful for the treatment of disorders and diseases related to injury to myelin and disorders and diseases related to inflammation. The disclosed oxysterols are oxidized derivatives of cholesterol. The disclosed oxysterols can be used to repair injured myelin by promoting oligodendrogenesis from neural stem cells and/or oligodendrocyte precursor cell populations. Injured myelin has been implicated in a number of different diseases and disorders including, but not limited to, neonatal brain injury, traumatic brain injury, spinal cord injury, cerebral palsy, seizures, cognitive delay, multiple sclerosis, stroke, autism, leukodystrophy, schizophrenia, and bipolar disorder.

Initially, a perinatal mouse model of myelin injury was developed, which recapitulated the pathological features and motor dysfunction observed in cerebral palsy. Employment of this model led to the discovery of an injury to the cerebral neural stem cell population. Using lineage tracing experiments, it was discovered that these neural stem cells stopped producing oligodendrocytes and began producing astrocytes in response to injury. Spurred by these observations, it was postulated that there may be biological targets within the stem cell population that could redirect these stem cells back into the oligodendrocyte lineage and promote oligodendrocyte differentiation.

For example, the sonic hedgehog (SHH) signaling pathway has been shown to promote oligodendrogenesis in vitro and in vivo. In addition, oxysterols are natural ligands for the SHH pathway, and recent studies in fibroblast cell culture systems demonstrated that the oxysterols 20α-hydroxycholesterol and 22α-hydroxycholesterol can activate the SHH pathway via direct binding to smoothened (SMO). Once SMO is bound to the oxysterol, it is believed that the negative regulator Patched1 (PTCH1) cannot interact with SMO, resulting in SHH pathway activation and subsequent oligodendrogenesis.

Accordingly, compounds that promote oligodendrogenesis, such as the oxysterols of the present disclosure, can be useful in treating diseases related to myelin pathology.

The disclosed oxysterols can also be used to treat diseases that are related to inflammation. A disease is "related to inflammation" if at least one symptom or manifestation of the disease involves inflammation of one or more tissues or organs. Diseases related to inflammation that can be treated by oxysterols include, but are not limited to, necrotizing enterocolitis, mesenteric ischemia, inflammatory bowel diseases (e.g., Crohn's disease and ulcerative colitis), lymphocytic colitis, Celiac disease, Behcet's disease, rheumatoid arthritis, psoriasis, and autoimmune thyroid disease.

For example, Toll-like receptor 4 (TLR4) signaling leading to NFκB activation has been observed in animal models of necrotizing enterocolitis (NEC). Specifically, TLR4 signaling leads to an intestinal infiltration of CD4+IL-17+ lymphocyte populations (TH17) in human (NEC) cases. These TH17 populations appear to be required for the development of (NEC) in animal models. Oxysterols have been found that prevent TLR4-dependent NFκB activation in epithelial cells, and to prevent the polarization of naïve CD4 T cells into the TH17 population. NFκB activation and TH17 infiltration can lead to inflammation.

Accordingly, compounds that can augment NFκB activation and TH17 polarization, such as the oxysterols of the present disclosure, can be useful in treating diseases related to inflammation.

Furthermore, human breast milk may be an appropriate vehicle for the administration of oxysterol therapy to infants in need of such therapy. Multiple naturally occurring oxysterols are identified in human breast milk, increasing the viability of employing its use in therapies for neonatal brain injuries and related disorders and diseases, and for use in therapies for inflammation related disorders and diseases. Most infants born prematurely are typically administered human breast milk for nourishment. Because oxysterols can be used to promote oligodendrogenesis and healthy myelin, breast milk or infant formula supplemented with additional amounts of oxysterols may be beneficial for promoting brain development or reducing inflammation in prematurely born infants, regardless of suspected or known brain injury or inflammatory disease.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety.

The materials, methods, and examples disclosed herein are illustrative only and not intended to be limiting.

The term "oxidized derivative" as used herein, means a compound substituted with an oxygen containing group, such as, but not limited to, at least one of a hydroxyl, oxo, alkoxy, epoxy or carboxy group.

The term "parenterally," as used herein, refers to modes of administration which include intravenous, intramuscular, intraperitoneal, intradermal, subcutaneous, intraarticular injection, and infusion.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of," and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, *Handbook of Chemistry and Physics*, 75th Ed., inside cover, and specific functional groups are generally defined as described therein.

Additionally, general principles of organic chemistry, as well as specific functional moieties and reactivity, are described in *Organic Chemistry*, Thomas Sorrell, University Science Books, Sausalito, 1999; Smith and March, eds., *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3rd Edition, Cambridge University Press, Cambridge, 1987; the entire contents of each of which are incorporated herein by reference.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Oxysterols

Oxysterols are oxidized derivatives of cholesterol. Oxysterols useful for the methods and compositions of the present disclosure may be oxidized derivatives of cholesterol wherein cholesterol is oxidized at any carbon of cholesterol. Oxysterols useful for the methods and compositions of the present disclosure may be substituted with an oxygen-containing group, such as, but not limited to, at least one of a hydroxyl, oxo, alkoxy, epoxy or carboxy group.

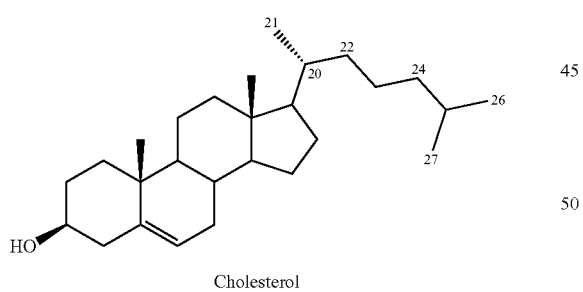

Cholesterol

Oxysterols may be important in many biological processes, including cholesterol homeostasis, atherosclerosis, sphingolipid metabolism, platelet aggregation, apoptosis, and protein prenylation, though their roles are often poorly understood. Oxysterols are lipophilic and cross the blood brain barrier. They are naturally present in small amounts in the brain and they are known ligands for the Liver X Receptor (LXR) and Sonic Hedgehog (SHH) signaling pathways. Oxysterols may be oxidized at sites on the tetracyclic ring structure or on the $C_{20\text{-}27}$ aliphatic chain. Specific oxysterols include the following:

20α-hydroxycholesterol 22-hydroxycholesterol 24-hydroxycholesterol 24-hydroxycholesterol 27-hydroxycholesterol Any oxysterol may be used in connection with the methods described herein. In certain embodiments, the oxysterol may be selected from the group consisting of: 20α-hydroxycholesterol; 22(R)-hydroxycholesterol; 22(S)-hydroxycholesterol; 24(R)-hydroxycholesterol; 24(S)-hydroxycholesterol; 25-hydroxycholesterol; and 27-hydroxycholesterol; or a pharmaceutically acceptable salt thereof.

In some embodiments, the oxysterol compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in *Pure Appl. Chem.*, 45: 13-30 (1976). The disclosure contemplates various stereoisomers and mixtures thereof and these are specifically included within the scope of this invention. Stereoisomers include enantiomers and diastereomers, and mixtures of enantiomers or diastereomers.

Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, (2) direct separation of the mixture of optical enantiomers on chiral chromatographic columns, or (3) fractional recrystallization methods.

It should be understood that the oxysterol compound may possess tautomeric forms, as well as geometric isomers, and that these also constitute an aspect of the invention.

The present disclosure also includes an isotopically-labeled compound, which is identical to the recited oxysterols, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in the disclosed oxysterols are $^{11}C$, $^{13}N$, $^{15}O$, and 18F. Isotopically-labeled oxysterols can generally be prepared by conventional techniques known to those skilled in the art or by processes analogous to those described in the accompanying Examples using appropriate isotopically-labeled reagent in place of non-isotopically-labeled reagent.

Oligodendrocytes and Oligodendrogenesis

Oxysterols of the present disclosure can promote the differentiation of oligodendrocytes from neural stem cells. Oligodendrocytes are a type of neuroglia. They function to provide support and insulation to axons in the central nervous system by creating the myelin sheath. Oligodendrocytes arise during development from oligodendrocyte precursor cells. Most oligodendrocytes develop during embryogenesis and early postnatal life from restricted periventricular germinal regions.

Oligodendrocytes are found in the central nervous system (CNS) and originate from the ventral ventricular zone of the embryonic spinal cord. They are the last cell type to be generated in the CNS. Myelination is only prevalent in a few brain regions at birth and continues into adulthood. The entire process is not complete until about 25-30 years of age.

As part of the nervous system, oligodendrocytes are closely related to nerve cells and provide a supporting role for neurons. In addition, the nervous system of mammals depends on myelin sheaths, which reduce ion leakage and decrease the capacitance of the cell membrane. Myelin also increases impulse speed, as saltatory propagation of action potentials occurs at the nodes of Ranvier in between Schwann cells (of the PNS) and oligodendrocytes (of the CNS).

Myelinating oligodendrocytes are a part of the white matter and myelination is an important component of intelligence.

Biomarkers of Oligodendrogenesis

Oligodendrogenesis may be determined by measuring the concentration of certain biomarkers in tissue. These biomarkers include, for example, Oligodendrocyte Transcription Factor (OLIG2), 2',3'-Cyclic-Nucleotide 3'-Phosphodiesterase (CNPase), and Myelin Basic Protein (MBP). The presence of, or an increase in the concentration of, these biomarkers may indicate oligodendrocyte formation.

a. Oligodendrocyte Transcription Factor

Oligodendrocyte transcription factor (OLIG2) is a basic helix-loop-helix transcription factor encoded by the Olig2 gene. The protein is of 329 amino acids in length, 32 kDa in size and contains 1 basic helix-loop-helix DNA-binding domain. The expression of OLIG2 is mostly restricted in central nervous system, and is well known for determining oligodendrocyte differentiation.

OLIG2 is mostly expressed in restricted domains of the brain and spinal cord ventricular zone which give rise to oligodendrocytes and specific types of neurons. During embryogenesis, OLIG2 first directs motor neuron fate by establishing a ventral domain of motor neuron progenitors and promoting neuronal differentiation. OLIG2 then switches to promoting the formation of oligodendrocyte precursors and oligodendrocyte differentiation at later stages of development.

b. 2',3'-Cyclic-nucleotide 3'-phosphodiesterase

2',3'-Cyclic-nucleotide 3'-phosphodiesterase (CNPase) is a myelin-associated enzyme that makes up 4% of total CNS myelin protein, and is thought to undergo significant age-associated changes. It is named for its ability to catalyze the phosphodiester hydrolysis of 2',3'-cyclic nucleotides to 2'-nucleotides, though a cohesive understanding of its specific physiologic functions are still ambiguous.

CNPase is expressed exclusively by oligodendrocytes in the CNS, and the appearance of CNPase seems to be one of the earliest events of oligodendrocyte differentiation. CNPase may play a critical role in the events leading up to myelination.

c. Myelin Basic Protein

Myelin basic protein (MBP) is important in the process of myelination of nerves in the nervous system. The myelin sheath is a multi-layered membrane, unique to the nervous system that functions as an insulator to greatly increase the velocity of axonal impulse conduction. MBP maintains the correct structure of myelin, interacting with the lipids in the myelin membrane.

The disclosed oxysterols can promote the formation of oligodendrocytes such that a treated subject has an increase of oligodendrocyte formation. The increase in oligodendrocyte formation may be measured relative to oligodendrocyte levels pretreatment in the subject. The increase of oligodendrocyte formation may be measured relative to oligodendrocyte levels in an untreated subject. The increase in oligodendrocyte formation may be measured relative to oligodendrocyte levels in an untreated control.

The disclosed oxysterols may promote an increase in oligodendrocyte formation of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 250%, at least 300%, at least 450%, or at least 500%.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

General Synthesis of Oxysterols

The disclosed oxysterols may be prepared by synthetic processes or by metabolic processes. Preparation of the compounds by metabolic processes includes those occurring in a human or animal body (in vivo) or processes occurring in vitro.

The compounds and intermediates may be synthesized, isolated, and purified by methods well-known to those skilled in the art of organic synthesis. Examples of conventional methods for isolating and purifying compounds include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described in, e.g., "Vogel's Textbook of Practical Organic Chemistry," 5th edition (1989), by Furniss, Hannaford, Smith, and Tatchell, Longman Scientific & Technical, Essex CM20 2JE, England.

A disclosed compound may have at least one basic atom or functional group, whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to, tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, glutamic acid, and the like.

Optimum reaction conditions and reaction times for each individual step can vary depending on the particular reactants employed and substituents present in the reactants used. Specific procedures are provided in the Examples section. Reactions can be worked up in the conventional manner, e.g., by eliminating the solvent from the residue and further purifying according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, *Protective Groups in Organic Synthesis* (4th ed.), John Wiley & Sons, NY (2006), which is incorporated herein by reference in its entirety.

Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

Pharmaceutical Compositions

The disclosed compounds may be incorporated into pharmaceutical compositions suitable for administration to a subject (such as a patient, which may be a human or non-human). The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the disclosure [e.g., an oxysterol] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of an oxysterol disclosed herein may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, about 90 mg/kg to about 100 mg/kg, or a range defined by any two of the foregoing values.

The pharmaceutical compositions may include pharmaceutically acceptable carriers. The term "pharmaceutically acceptable carrier," as used herein, refers to a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.).

Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, transdermal, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol, and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%/o.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben, and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. *Cosmetic Ingredient Handbook,* 1992, pp. 587-592; *Remington's Pharmaceutical Sciences,* 15th Ed. 1975, pp. 335-337; and McCutcheon's Volume 1, *Emulsifiers & Detergents,* 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active agent (e.g., an oxysterol) and 50% to 99.99% of one or more carriers. Compositions for parenteral administration typically include 0.1% to 10% of active agent and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof. Capsules (including implants, time release and sustained release formulations) typically include an active compound (e.g., an oxysterol), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G.M.B.H. of Darmstadt, Germany), waxes, and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid compositions, which may be administered orally, may include an oxysterol compound disclosed herein and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal, and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: an oxysterol compound as disclosed herein and a carrier. The carrier of the topical composition preferably aids penetration of the compounds into the skin. The carrier may further include one or more optional components. Transdermal administration may be used to facilitate delivery. Such transdermal administration may bypass any gut metabolism, whereby microbes may use one or more oxysterols as substrates. Transdermal administration may be in the absence of carbohydrates to avoid administering bacterial substrates that may negatively impact gut health. Accordingly, transdermal administration, via patches for example, may facilitate controlled release delivery that can bypass any metabolism that resides along the digestive tract, for example in the gut.

The amount of the carrier employed in conjunction with a disclosed compound is sufficient to provide a practical quantity of composition for administration per unit dose of the medicament. Techniques and compositions for making dosage forms useful in the methods disclosed herein are described in the following references: *Modern Pharmaceu-*

*tics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to about 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

In one embodiment, the pharmaceutical composition may include human breast milk. The active pharmaceutical ingredient may be a component of human breast milk. The human breast milk may thus be administered to a subject in need of the active pharmaceutical ingredient. Some infants may not be able to take food or medication by mouth. For example, infants with acute brain injury are critically ill and may not be able to take food or medication by mouth. The infants may also need bowel rest. Accordingly, in one embodiment, total parenteral nutrition (TPN) may be administered through a central line. TPN contains the hydration and nutrients needed to sustain life and grow the infant. Calories may be delivered via carbohydrates, protein, and lipids. The lipids may be administered as an intralipid emulsion.

Oxysterol therapy may be added to the intralipid emulsion for intravenous administration, for example, through a central line. Intralipid emulsions are commercially available. An example of a commercially available intralipid emulsion is a 20% fat emulsion containing soybean oil, egg yolk, phospholipids, and glycerin. Other formulations that may be supplemented with oxysterols include INTRALIPID® 20% (Baxter Healthcare Corp., Deerfield, Ill.) and SMOFLIPID® (Fresenius Kabi, Bad Homburg vor der Höhe, Germany), for example. Intravenous administration of oxysterol preparations in fat emulsions may also bypass the negative effects of oxysterol metabolism in the gut.

Methods of Treatment

1. Myelin Related Diseases or Disorders

The disclosed oxysterols and compositions may be used in methods for treatment of disorders and diseases related to brain injury, in particular, injury to myelin. The methods of treatment may comprise administering to a subject in need of such treatment a composition comprising a therapeutically effective amount of an oxysterol. These methods promote the formation of oligodendrocytes, which are cells which function to provide support and insulation to axons in the central nervous system by creating the myelin sheath. Thus, the formation of oligodendrocytes may serve to create myelin and repair damaged myelin in subjects with injured myelin.

The compositions may be useful for treating and preventing certain diseases and disorders in humans and animals related to myelin injury. Treatment or prevention of such diseases and disorders can be effected by promoting oligodendrogenesis in a subject, by administering a compound or composition of the disclosure, either alone or in combination with another active agent as part of a therapeutic regimen to a subject in need thereof.

Diseases and/or disorders which may be treated and/or prevented by the disclosed methods include neonatal brain injury, traumatic brain injury, spinal cord injury, cerebral palsy, seizures, cognitive delay, multiple sclerosis, stroke, autism, leukodystrophy, schizophrenia, and bipolar disorder. The neonatal brain injury may include at least one of diffuse white matter injury, periventricular leukomalacia (PVL), hypoxic-ischemic encephalopathy (HIE), neonatal stroke, and grade 3-4 intraventricular hemorrhages (IVH).

2. Inflammation Related Disease or Disorders

The disclosed oxysterols and compositions may be used in methods for treatment of disorders and diseases related to inflammation. The methods of treatment may comprise administering to a subject in need of such treatment a composition comprising a therapeutically effective amount of an oxysterol. These methods augment NFκB activation and TH17 polarization. Thus, augmenting NFκB activation and TH17 polarization may serve to reduce inflammation and reduce inflammation related damage in subjects with inflammatory diseases or disorders.

The compositions may be useful for treating and preventing certain diseases and disorders in humans and animals related to inflammation. Treatment or prevention of such diseases and disorders can be effected by augmenting NFκB activation and TH17 polarization in a subject, by administering a compound or composition as described herein, either alone or in combination with another active agent as part of a therapeutic regimen to a subject in need thereof.

Diseases and/or disorders which may be treated and/or prevented by the disclosed methods include necrotizing enterocolitis, mesenteric ischemia, inflammatory bowel diseases including Crohn's disease and ulcerative colitis, lymphocytic colitis, Celiac disease, Behcet's disease, rheumatoid arthritis, psoriasis, and autoimmune thyroid disease.

a. Necrotizing Enterocolitis

Necrotizing enterocolitis (NEC) remains a leading cause of death and morbidity in premature infants in the neonatal intensive care unit, and it is the most common cause of surgical emergencies within this population. Prematurity and low birth weight are the leading risk factors for the development of NEC. The disease is characterized by bowel wall injury and/or necrosis, inflammation of the bowel, and subsequent invasion of the bowel wall with gut microbes leading to sepsis.

b. Mesenteric Ischemia

Mesenteric ischemia is an acute or chronic condition affecting the digestive tract, in which the blood supply to the digestive tract is decreased. Acute mesenteric ischemia occurs suddenly as a result of a blockage to the flow if oxygen-rich blood and can cause permanent damage to the intestines. Chronic mesenteric ischemia occurs gradually and from narrowing in one or more of the arteries supplying blood to the intestines. Symptoms of mesenteric ischemia include, for example, pain after eating, change in bowel movements, diarrhea, rectal bleeding, constipation, bloating, nausea, vomiting, and weight loss. Inflammation and injury to the intestines can result from the inadequate blood supply.

c. Crohn's Disease

Crohn's disease is a chronic inflammatory disease that may affect any part of the gastrointestinal tract. The inflammation can cause pain, severe diarrhea, fatigue, weight loss, and malnutrition. Complications outside of the digestive tract that may occur in Crohn's disease include, for example, anemia, skin rashes, arthritis, and inflammation of the eye. Crohn's disease can be debilitating and may lead to life-threatening complications. Bowel obstruction can occur, and subjects with Crohn's disease are at a greater risk for developing cancer of the gastrointestinal tract.

d. Ulcerative Colitis

Ulcerative colitis is a chronic disease that causes inflammation of the large intestine. Ulcers commonly occur on the inner lining of the large intestine. Symptoms of ulcerative colitis can include pain, severe diarrhea, rectal bleeding, nausea or loss of appetite, fever, anemia, weight loss, and nutritional deficiency. Joint pain, eye irritation, and rashes may also occur in subjects with ulcerative colitis. The symptoms typically occur intermittently with periods of mild or no symptoms between flares. Subjects with ulcerative colitis have an increased risk of colorectal cancer.

e. Lymphocytic Colitis

Lymphocytic colitis is a subtype of microscopic colitis, and is a condition that causes inflammation of the colon. Symptoms of lymphocytic colitis include, for example, abdominal pain, cramping, and diarrhea that is continuous or episodic.

f. Celiac Disease

Celiac disease is an autoimmune disease, in which the immune system mounts a response to the presence of the gluten protein. The immune response attacks the micro-villi that line the small intestine, and causes inflammation in the small intestine. The intestinal damage can lead to diarrhea, fatigue, weight loss, malabsorption, bloating, mouth ulcers, and anemia. Lactose intolerance can also develop as a result to the damage to the intestines. Celiac disease leads to an increased risk for adenocarcinoma and lymphoma. The associated malabsorption can lead to a number of additional symptoms, including abnormal coagulation, and osteopenia. Additional symptoms of celiac disease include dermatitis herpetiformis, growth failure, puberty delay, and pregnancy complications.

g. Behcet's Disease

Behcet's disease is a chronic, autoimmune, autoinflammatory disorder, which is systemic. Symptoms include, for example, oral ulcers, genital ulcers, inflammation of the eye, skin lesions, and arthritis. Inflammation of the uvea, retina, and/or iris of the eye may lead to blindness.

Additional symptoms can include blood clots, inflammation of the central nervous system, and inflammation and ulceration throughout the digestive tract. The inflammation of the digestive tract may lead to abdominal pain, diarrhea, lack of appetite, weight loss, and bleeding of the rectum.

h. Rheumatoid Arthritis

Rheumatoid arthritis is a chronic inflammatory disorder that can affect joints and other body systems, including the skin, eyes, lungs, heart, and blood vessels. Symptoms of rheumatoid arthritis can include warm, swollen, and painful joints. The associated synovitis can cause tethering of tissue, which leads to loss of movement of the joint, and erosion of the joint surface, causing deformity. Subjects with rheumatoid arthritis commonly develop rheumatoid nodules, which are due to a type of inflammatory reaction known to pathologists as a necrotizing granuloma. Vasculitis, pyoderma gangrenosum, thinning of the skin, palmar erythema, and erythema nodosum are also skin manifestations of rheumatoid arthritis. Symptoms of the lungs can include fibrosis, pleural effusions, and inflammation of the lungs. Cardiac symptoms can include atherosclerosis, myocardial infarction, stroke, pericarditis, endocarditis, fibrosis, and inflammation surrounding the heart. Renal amyloidosis can occur, due to chronic inflammation.

i. Psoriasis

Psoriasis is an autoimmune disease that is characterized by abnormal patches of skin. The affected patches of skin are typically red, scaly, and itchy. Koeber phenomenon can occur, due to psoriatic changes of the skin. Psoriasis vulgaris (also known as chronic stationary psoriasis or plaque-like psoriasis) is the most common form, and causes silvery-white scaly patches on the skin. These patches most commonly occur on skin of the elbows, knees, scalp, and back. Pustular psoriasis appears as raised bumps filled with non-infectious pus. Psoriatic arthritis is a form of chronic inflammatory arthritis, and frequently occurs in combination with psoriasis of the nails and skin. Psoriatic arthritis can affect the joints of the fingers, toes, hips, knees, spine, and sacroiliac joint.

j. Autoimmune Thyroid Disease

Autoimmune thyroid disease is a chronic inflammatory disorder of the thyroid gland. This disease can also affect the hormones produced by the thyroid gland, such as Triiodothyronine (T3), thyroxine (T4), and thyroid stimulating hormone (TSH). Autoimmune thyroid disease can cause hyperthyroidism, which leads to excessive sweating, rapid heart rate, anxiety, tremors, fatigue, difficulty sleeping, sudden weight loss, and protruding eyes.

Autoimmune thyroid disease can also cause hypothyroidism, which leads to weight gain, fatigue, dry skin, hair loss, intolerance to cold, and constipation. Goiters may be present with autoimmune thyroid disease. Grave's disease and Hashimoto's disease are forms of autoimmune thyroid disease.

Therefore, it would be beneficial to administer oxysterol therapy to subjects who suffer from necrotizing enterocolitis, mesenteric ischemia, inflammatory bowel diseases including Crohn's disease and ulcerative colitis, lymphocytic colitis, Celiac disease, Behcet's disease, rheumatoid arthritis, psoriasis, autoimmune thyroid disease, as well as other diseases or disorders associated with inflammation that are known in the art.

Modes of Administration

Methods of treatment may include any number of modes of administering the disclosed oxysterol or composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire®). In the pharmaceutical composition, the agent may also be dispersed in a microparticle, e.g. a nanoparticulate composition. Any formulation or preparation described herein may or may not contain carbohydrates.

For parenteral administration, the agent can be dissolved or suspended in a physiologically acceptable diluent, such as, e.g., water, buffer, oils with or without solubilizers, surface-active agents, dispersants, or emulsifiers. Suitable oils include, for example, olive oil, peanut oil, cottonseed oil, soybean oil, castor oil, and sesame oil. More generally, for parenteral administration, the agent can be in the form of an aqueous, lipid, oily or other kind of solution or suspension or even administered in the form of liposomes or nano-suspensions. Other formulations include INTRALIPID® 20% (Baxter Healthcare Corp., Deerfield, Ill.) and SMOFLIPID® (Fresenius Kabi, Bad Homburg vor der Höhe, Germany), for example.

In an embodiment, one or more oxysterol compounds may be administered in a composition comprising human breast milk. The human breast milk may thus be administered orally to a subject in need of oxysterol therapy. The human breast milk may be further supplemented with oxysterols in addition to oxysterols that are naturally present in human breast milk. The oxysterols used for supplementation may be higher doses of one or more oxysterols already present or they may be one or more oxysterols not found to be naturally occurring in human breast milk. In one embodiment, the oxysterols may be 20α-hydroxycholesterol and/or 24-hydroxycholesterol.

In another embodiment, one or more oxysterols may be administered in a composition comprising infant formula (e.g., the infant formula may further comprise at least one oxysterol). Infant formula is a manufactured food which purports to be or is represented for special dietary use solely as a food for infants by reason of its simulation of human milk or its suitability as a complete or partial substitute for human milk. The infant formula may thus be administered orally to a subject in need of oxysterol therapy.

In addition, human breast milk or infant formula comprising at least one oxysterol may be administered to prematurely born infants, regardless of suspected or known inflammatory disease or disorder. Because oxysterols can be used to augment NFκB activation and TH17 polarization, breast milk or infant formula supplemented with additional amounts of oxysterols may be beneficial for reducing inflammation and/or inflammation related damage in infants with inflammatory diseases or disorders.

Infant formula which may be suitable for the methods described herein include, but are not limited to, milk-based formula (for example, SIMILAC®, ENFAMIL®, or GERBER GOOD START®), soy-based formula or lactose-free (for example, SIMILAC SOY ISOMIL®, ENFAMIL PROSOBEE®, GERBER GOOD START SOY®), partially or extensively hydrolyzed formulas (for example, ENFAMIL GENTLEASE®, NUTRAMIGEN®), and formula specially designed for prematurely born infants (for example, NEOSURE®, ENFACARE®).

Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to an oxysterol. The above combinations include combinations of a compound of the present invention not only with one other active compound, but also with two or more other active compounds.

In certain embodiments, the oxysterol can be combined with one or more anti-inflammatory agents or immunosuppressive agents (also referred to as "immunosuppressants"), a variety of which are known in the art. For example, the oxysterol may be administered in combination with corticosteroids (e.g., prednisone and fluticasone), non-steroidal anti-inflammatory drugs (NSAIDs) (e.g., aspirin, ibuprofen, and naproxen), disease-modifying antirheumatic drugs (DMARDs) (e.g., methotrexate, sulfasalazine, leflunomide, azathioprine, and cyclophosphamide), biologic drugs (e.g., infliximab, etanercept, adalimumab, certolizumab, golimumab, abatacept, tocilizumab, and rituximab), alkylating agents, cyclosporin, tacrolimus, sirolimus, everolimus, interferons, opioids, TNF binding proteins, myocphenoalte, and/or other small biological agents (e.g., fingolimod and myriocin).

For the treatment of necrotizing enterocolitis, oxysterols can be combined with a variety of antibiotics. The antibiotics include, but are not limited to, ampicillin, gentamycin, zosyn, vancomycin, or a combination thereof. In addition, the subject would ingest nothing by mouth for 10 days after abdominal x-rays have been normalized.

For the treatment of Crohn's disease, ulcerative colitis, lymphocytic colitis, Celiac Disease, Behcet's disease, autoimmune thyroid disease, and rheumatoid arthritis, oxysterols can be combined with immunosuppressive therapies, especially during disease flare-ups, for example. Immunosuppressive therapies include those described above, including corticosteroids, azathioprine (IMURAN®), mercaptopurine, or a combination thereof. Selective biologic agents can also be coadministered with oxysterols and include, but are not limited to infliximab (REMICADE®), adalimumab (HUMIRA®), and certolizumab pegol (CIMZIA®).

For psoriasis, oxysterols may be directly applied to the skin lesions, combined with, for example, corticosteroids, vitamin D, retinoids, phototherapy, immunosuppressants (e.g., methotrexate or cyclosporine), or a combination thereof.

The disclosed compounds may be included in kits comprising the compound (e.g., one or more oxysterols), a systemic or topical composition described above, or both; and information, instructions, or both, that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

Evaluation of Treatment

To determine the efficacy of oxysterol treatment for diseases or disorders related to inflammation, the levels of macrophage/NFκB or T cell/TH17 may be evaluated using suitable method known in the art for measuring such proteins.

Quantification of oligodendrocyte cell numbers in the brain is critical to determining the impact of oxysterol therapy. Stereology is a useful research tool used by neuroscientists to provide accurate and unbiased estimates of cell numbers within specified brain regions. The number of oligodendrocyte numbers is determined using Stereo Investigator™ software (MBF Bioscience) and a Zeiss Axiolmager M2 motorized fluorescent microscope with Apotome structured illumination. The detection of differences in locomotor function is an important tool for the assessment of the severity of many conditions that affect the central nervous system (CNS), peripheral nervous system (PNS) and skeletal structures or muscles. A gait analysis system, such as the CatWalk™ XT, provides automatic and sensitive detection of a full range of parameters related to footprints and the dynamics of gait in animal testing. Methods for determining the impact of oxysterol therapy are further described in, e.g., International Patent Application Publication WO 2016/007762.

The compounds and processes of the invention will be better understood by reference to the following examples, which are intended as an illustration of and not a limitation upon the scope of the invention.

EXAMPLES

20α-Hydroxycholesterol (20HC) and 22α-hydroxycholesterol were purchased commercially from Sigma-Aldrich. All oxysterols were resuspended in DMSO at 12 mM for use in cell culture systems. In vivo studies utilized oxysterols freshly dissolved in corn oil prior to administration.

Example 1

This example demonstrates the efficacy of 25-hydroxycholesterol therapy.

Figure 1A:
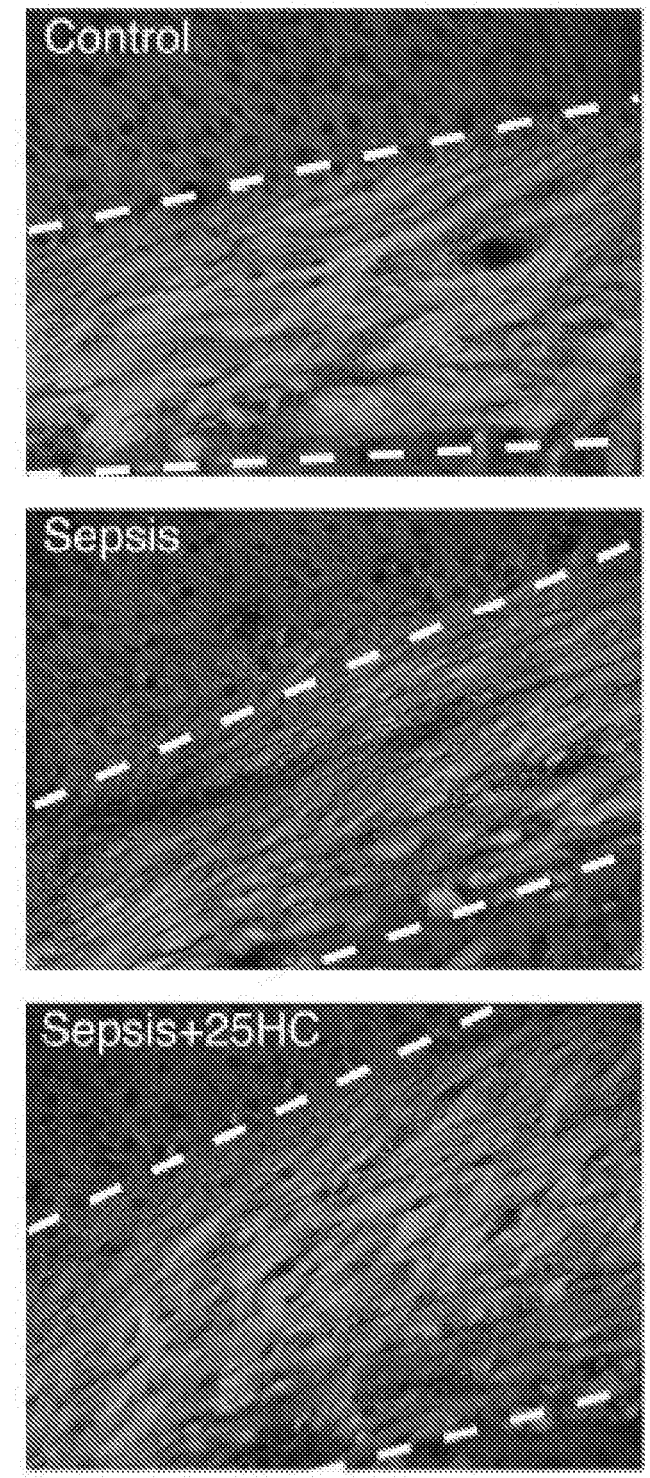
FIG. 1A is a series of images of fluoromyelin (Invitrogen) staining of myelin, which show decreased myelination of the corpus callosum (dashed lines) in sepsis mice at p25.
Figure 1B:
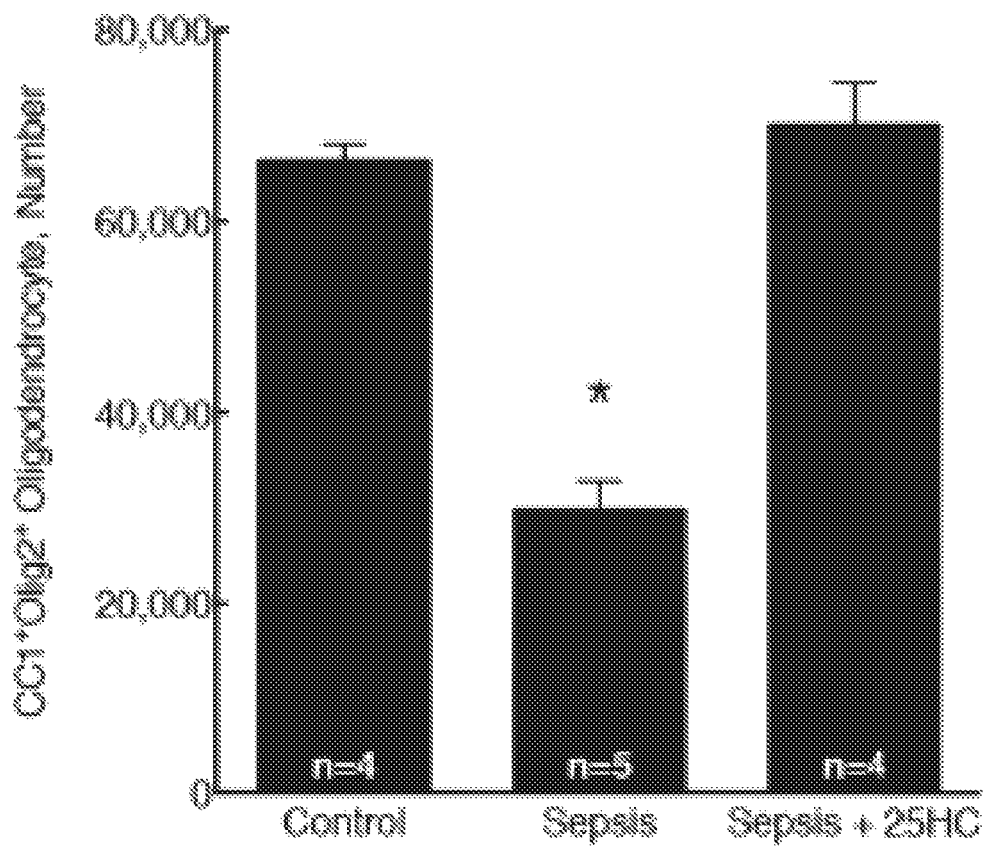
FIG. 1B is a quantification of the number of mature oligodendrocytes in 25HC-treated mice and septic injured mice.

Perinatal bowel perforation is a common complication of premature birth and is strongly linked to myelin injury and cerebral palsy. A mouse model of perinatal white matter injury was developed. The model simulates a perinatal bowel perforation and sepsis by injection of donor cecal contents into the peritoneal cavity of neonatal mice on postnatal day 5. Using this model, the efficacy of 25-hydroxycholesterol in reversing white matter injury was tested. Mice treated with 100 mg/kg/day of 25-hydroxycholesterol for five days showed improved myelin integrity, compared to septic injured mice that received a vehicle control (FIG. 1A). Breast-milk associated 25-HC reversed diffuse white matter injury. The cells were stained with oligodendrocyte marker CC1. 40× high power fields (PHF) were imaged. Using a stereology approach to quantify oligodendrocytes, it was determined that 25HC-treated mice had significantly higher ($p<0.0001$) numbers of mature oligodendrocytes (CC1+Olig2+), when compared to septic injured mice (FIG. 1B).

Example 2

Figure 2A:
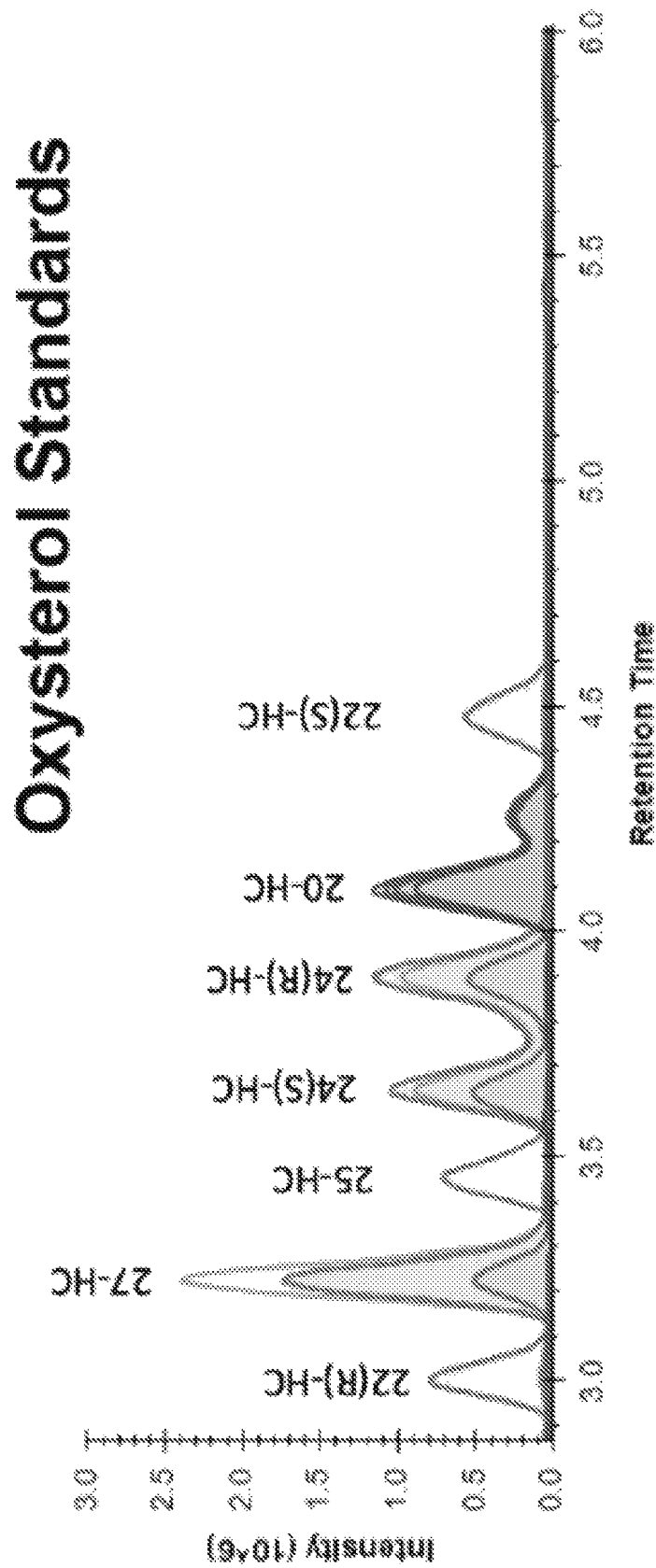
FIG. 2A is a graph showing results of mass spectrometry experiments to analyze oxysterol standards.
Figure 2B:
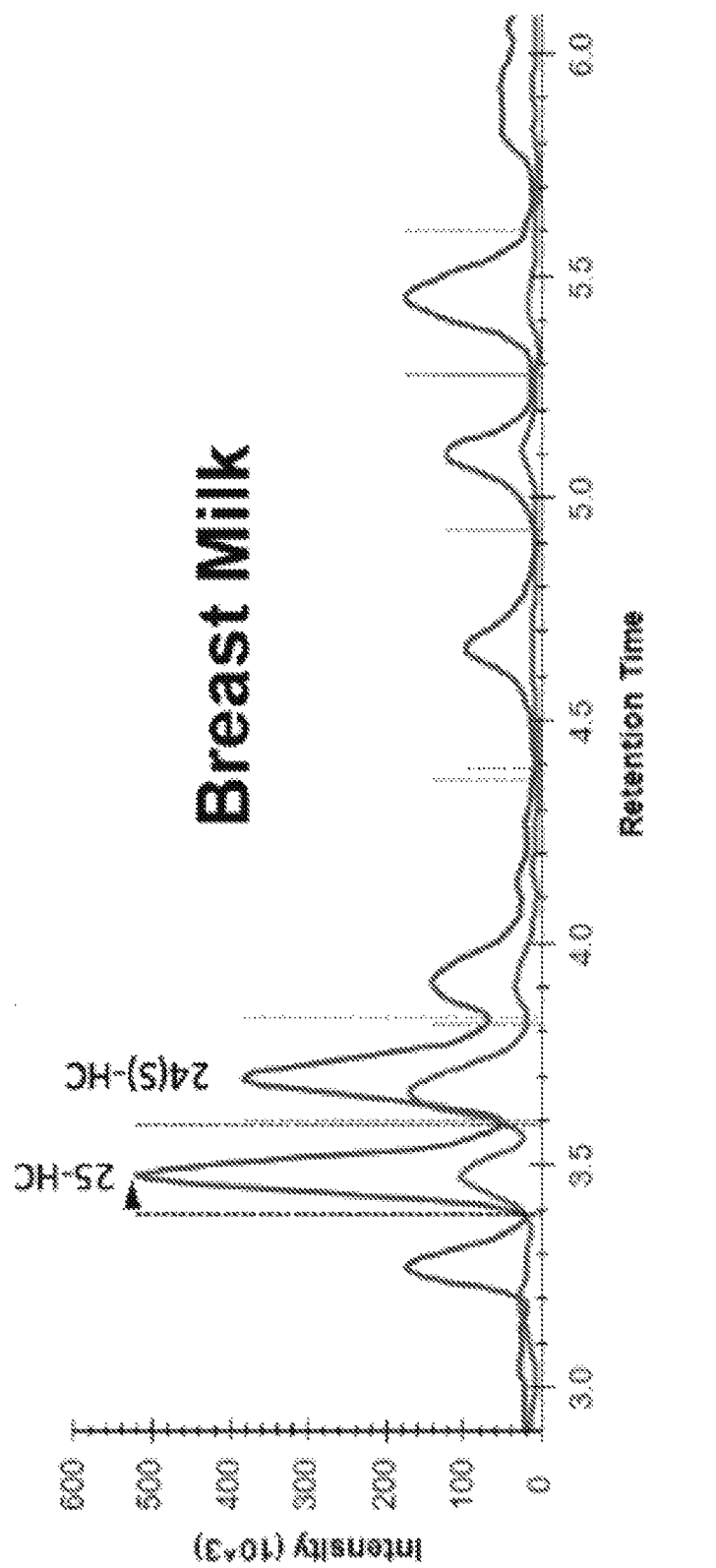
FIG. 2B is a graph depicting the measurement of different oxysterols in human breast milk.
Figure 3:
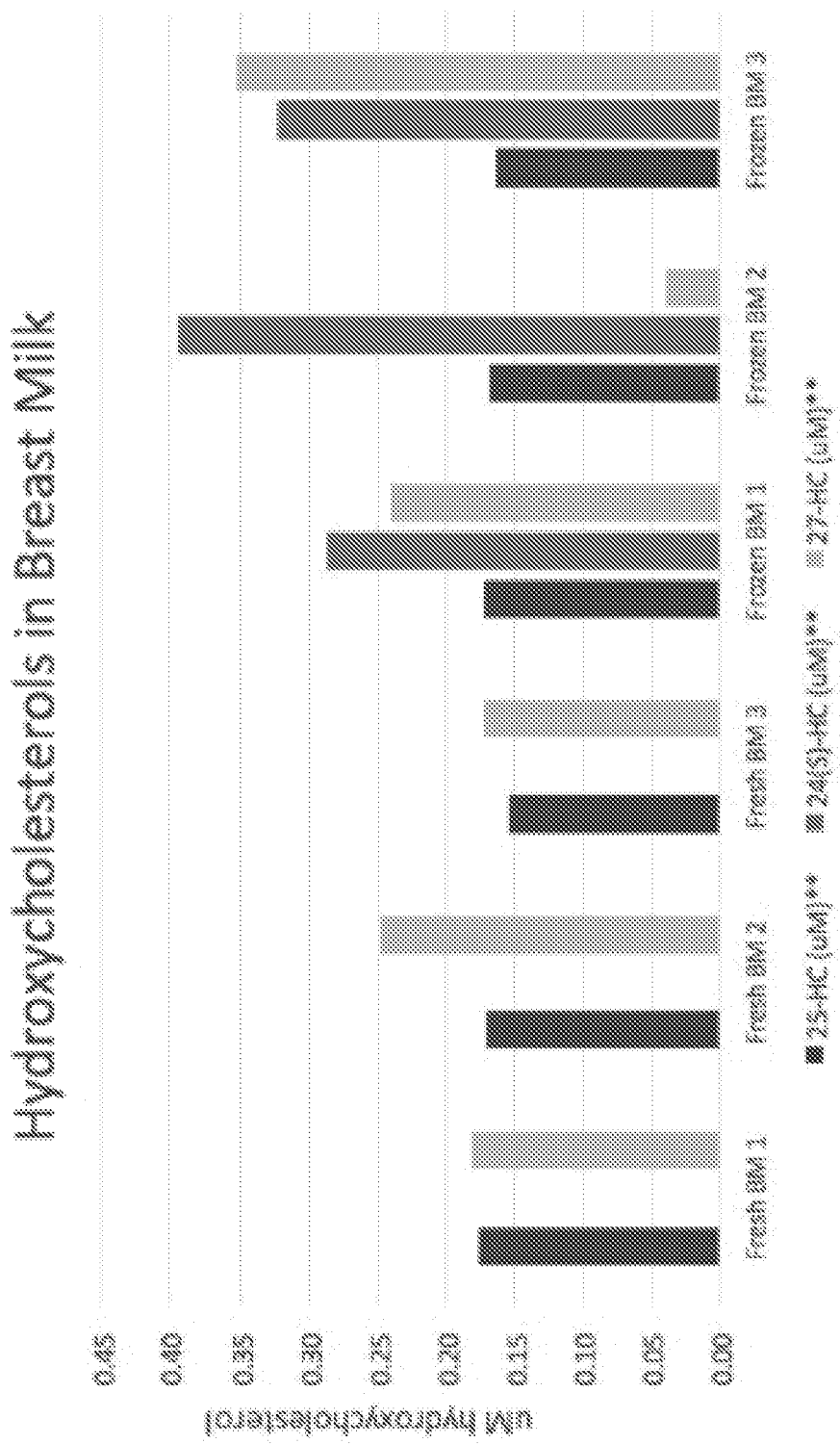
FIG. 3 is a graph depicting the measurement of different oxysterol concentrations in human breast milk.
Figure 4A:
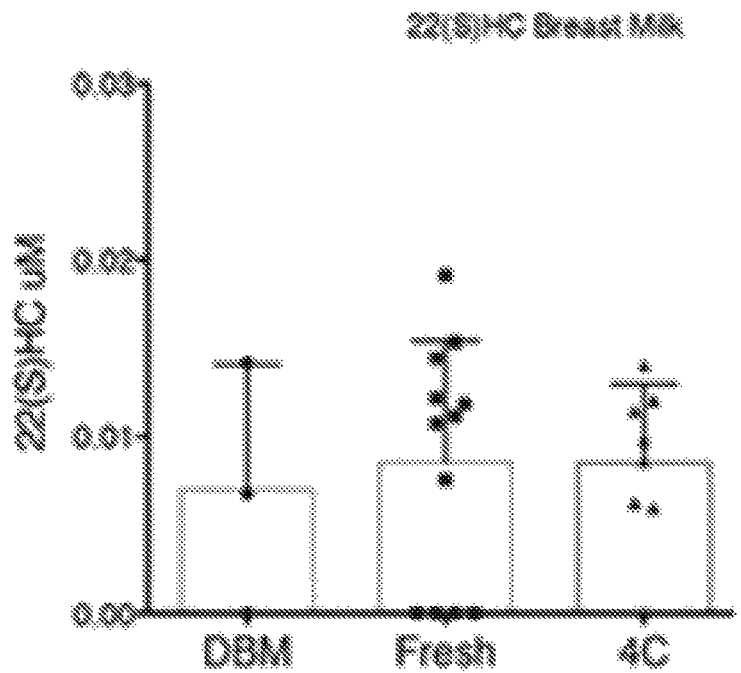
FIG. 4A is a graph illustrating the results of liquid chromatography tandem-mass spectrometry analysis of oxysterols in human breast milk, which shows detection of 22(S)HC.
Figure 4B:
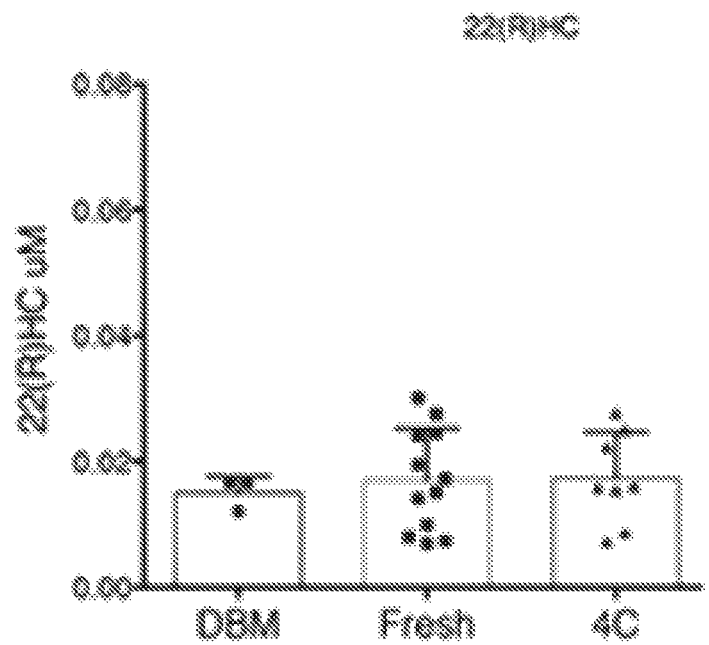
FIG. 4B is a graph illustrating the results of liquid chromatography tandem-mass spectrometry analysis of oxysterols in human breast milk, which shows detection of 22(R)HC.
Figure 4C:
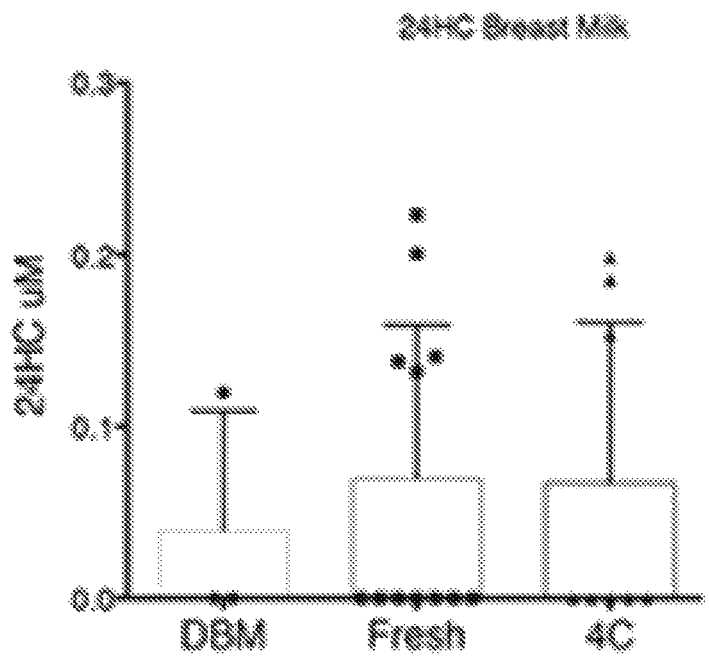
FIG. 4C is a graph illustrating the results of liquid chromatography tandem-mass spectrometry analysis of oxysterols in human breast milk, which shows detection of 24HC.
Figure 4D:
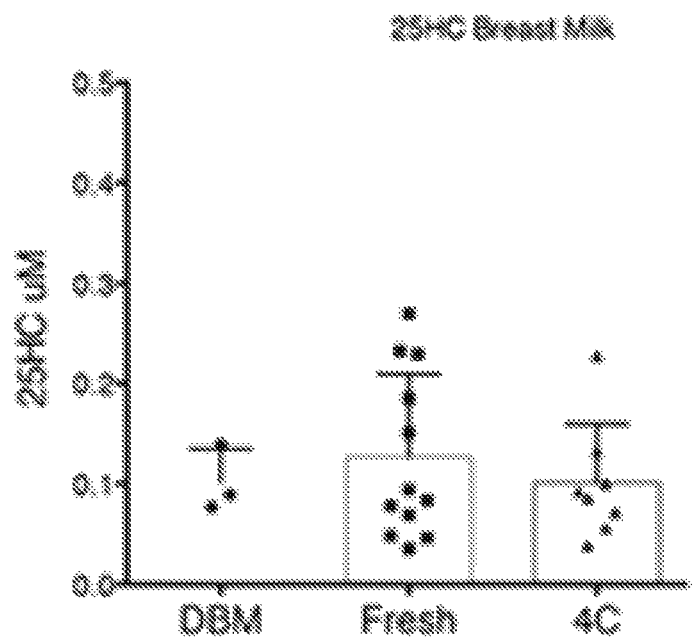
FIG. 4D is a graph illustrating the results of liquid chromatography tandem-mass spectrometry analysis of oxysterols in human breast milk, which shows detection of 25HC.
Figure 4E:
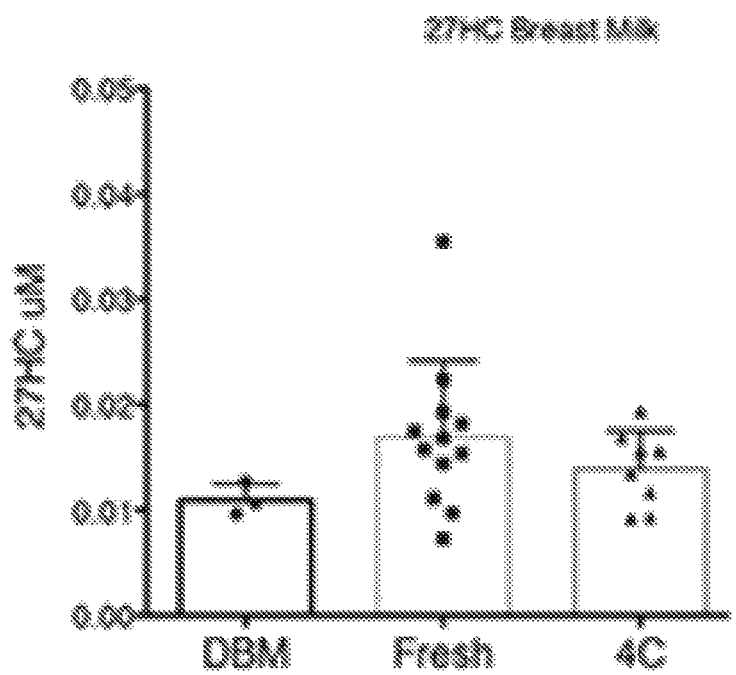
FIG. 4E is a graph illustrating the results of liquid chromatography tandem-mass spectrometry analysis of oxysterols in human breast milk, which shows detection of 27HC.
Figure 4F:
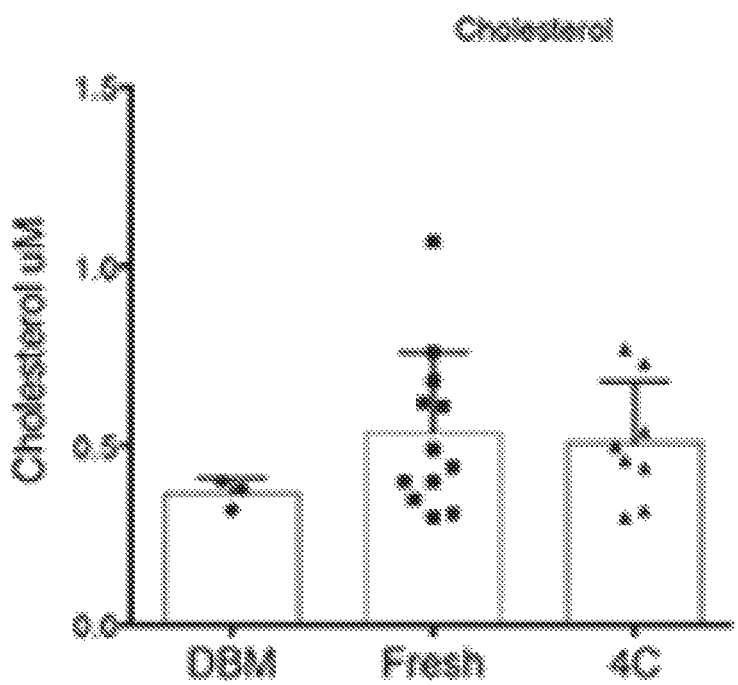
FIG. 4F is a graph illustrating the results of liquid chromatography tandem-mass spectrometry analysis of oxysterols in human breast milk, which shows detection of cholesterol.

This example demonstrates mass spectroscopy detection of oxysterols in human breast milk. Mass spectrometry assays were employed to identify oxysterols that are present in human breast milk. Samples of freshly pumped human breast milk were obtained. Half of each sample was immediately frozen on dry ice and stored at −80° C. The remainder was stored at 4° C. for six days before analysis. Breast milk samples were then analyzed by mass spectrometry and compared to oxysterols standards (FIGS. 2A,B). While 20α-hydroxycholesterol was not detected in human breast milk, abundant levels of 24-hydroxycholesterol (24HC), 25-hydroxycholesterol (25HC), and 27-hydroxycholesterol (27HC) were observed (FIG. 3).

Example 3

This example demonstrates liquid chromatography tandem mass spectrometry detection of oxysterols in human breast milk.

Liquid chromatography tandem mass spectrometry was employed to identify oxysterols that are present in human breast milk. The samples were from freshly pumped human breast milk from mothers who recently delivered healthy, full-term infants. A portion of the milk was frozen immediately, and a portion was stored at 40° C. for 48 hours prior to freezing to determine oxysterol stability in milk. In addition to freshly pumped milk, pasteurized human breast milk from a donor breast milk bank was also analyzed. While 20α-hydroxycholesterol was not detected in any of the milk samples, 22-hydroxycholesterol (22HC), 24-hydroxycholesterol (24HC), 25-hydroxycholesterol (25HC), and 27-hydroxycholesterol (27HC) were detected in multiple samples (FIG. 4). Storage at 40° C. for 48 did not impact levels of oxysterols.

Example 4

This example demonstrates in vitro oligodendrocyte differentiation from neural stem cells with breast milk-associated 24-hydroxycholesterol and 25-hydroxycholesterol.

Primary neural stem cells were treated with 24-hydroxycholesterol and 25-hydroxycholesterol at 1 μm and 0.5 μm for five days, then allowed to differentiate for 18 days. Protein lysates were probed for oligodendrocyte-associated proteins CNPase and myelin basic protein (MBP). Exposure of neural stem cells to these oxysterols induced expression of oligodendrocyte-associated proteins CNPase and MBP, suggesting similar activity as 20α-hydroxycholesterol (FIG. 5).

Example 5

This example demonstrates an in vitro screening method for oligodendrogenesis.

Primary neural stem cells generated from mice were screened for oligodendrogenic potential after treatment with 20HC, 22HC, 24HC, 25HC, and 27HC. Neural stem cells in 8-well chamber slides were exposed to the indicated oxysterol for five days, and then allowed to differentiate for 15-18 days. Following differentiation, cells were fixed and stained for oligodendrocyte markers CNPase and myelin basic protein (MBP) (FIG. 6A). Stained cells were randomly sampled with a 40× objective, using Stereo Investigator software to eliminate bias, while quantifying the number of oligodendrocytes. Each condition was sampled at 10-12 computer selected sites. Images were used to count the number of nucleated CNPase+ cells per high power field (HPF). An increased number of oligodendrocytes was found in cultures exposed to 20HC, 22HC, 24HC, and 25HC compared to media control. 27HC and Oxo16 (oxysterol with no known hedgehog activity) did not increase the number of oligodendrocytes in culture (FIG. 6B).

Example 5

This example demonstrates that 20α-hydroxycholesterol blocks NF-κB activation in mononuclear phagocytes.

Splenocytes where harvested from postnatal day 12 mice. Monocytes were negatively selected using anti-CD3, CD19 magnetic beads. Cells were treated with vehicle control (DMSO) or 1 μm 20HC for 24 hours. After exposure to 20HC, monocytes were treated with 500 ng/mL of lipopolysaccharide (LPS) to activate the TLR4 receptor and activate NF-κB. Compared to control cells, LPS-treated cells degraded I-κB and phosphorylated p65 consistent with NF-κB activation (FIG. 7). I-κB degradation and phosphorylation of p65 was blocked in 20HC-treated monocytes.

Example 6

This example demonstrates that 20HC and 24HC block TH17 polarization of naïve CD4+ T cells in vitro.

Naïve CD4 T cells were isolated from rodent spleen tissue using CD4 magnetic beads. CD4+ lymphocytes were cultured on plates coated with anti-CD3 antibody and anti-CD28 antibodies in the presence of rTGFb, rIL-6, and rIL-23 for 5 days. Four hours prior to flow cytometry analysis, the cells were stimulated with PMA, ionomycin, and Brefeldin A. The cells were then analyzed for IL-17 production (FIG. 8, wherein CD4+ T cell culture in the presence of CD3/CD28-coated beads with IMDM media containing rTGFβ (4 ng/ml), rIL-6 (20 ng/ml), rIL-23 (50 ng/ml), anti-IL-4 Ab, and anti-IFNg Ab with or without GW or HC for 5 days. PMA (50 ng/ml), Ionomycin (500 ng/ml) for 5 h, and Brefeldin A (10 μg/ml) for last 3 h)). 7.8% of the control cells polarized into the TH17 population. The LXR agonist GW3965 prevented TH17 polarization (2.6%). Breast milk associated oxysterols 20HC and 24HC also prevented TH17 polarization (2.2% and 2.1% respectively). 25HC promoted TH17 production at low doses (23.6%) and inhibited production at higher doses (2.7%).

Example 7

This example demonstrates that pretreatment of mice with 20HC blocks the development of multiple sclerosis-like symptoms in an experimental allergic encephalitis (EAE) mouse model.

EAE was induced using myelin oligodendrocyte glycoprotein (MOG35-55) peptide using standard approaches (see, e.g., Bittner et al., *J. Vis. Exp.*, 86: 51275 (2014); and Miller et al., *Curr Protoc Immunol.*, Unit-15.1 (2007)) in 15 wild-type 8 week old C57BL/6J mice. TH17 T cell populations are pathogenic in the EAE model and have been implicated in multiple sclerosis (MS). Seven mice (3 male, 4 female) proceeded without further intervention while 8 mice (3 female and 5 male) were given daily 125 μL subcutaneous injections of 20HC resuspended in corn oil (10 mg/mL) two days prior to EAE induction and through day 14, just prior to peak clinical severity. Mice were scored daily for the development of ascending paralysis that is indicative of the development of EAE. In vivo treatment of mice with 20HC (50 mg/kg/day) disrupted the development of MS-like symptoms in the EAE model, as shown in FIGS. 9A and 9B.

Thus, the results of this example demonstrate that 20HC protects mice against the development of EAE, most likely by blocking TH17 T cell polarization in vivo.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the present disclosure are set out in the following numbered clauses:

Clause 1. A method of treating diseases or disorders related to inflammation in a subject in need thereof, the method comprising administering a therapeutically effective amount of at least one oxysterol.

Clause 2. The method of clause 1, wherein the oxysterol augments NF☐B activation and TH17 polarization, thereby reducing inflammation in the subject.

Clause 3. The method of clause 1, wherein the oxysterol reduces TH17 polarization, thereby reducing inflammation in the subject.

Clause 4. The method of clause 1, wherein the oxysterol reduces NF☐B activation.

Clause 5. The method of clause 1, wherein the oxysterol comprises a cholesterol derivative oxidized at any of carbons 20-27.

Clause 6. The method of clause 1, wherein the oxysterol is selected from the group consisting of: 20α-hydroxycholesterol; 22(R)-hydroxycholesterol; 22(S)-hydroxycholesterol; 24(R)-hydroxycholesterol; 24(S)-hydroxycholesterol; 25-hydroxycholesterol; and 27-hydroxycholesterol; or a pharmaceutically acceptable salt thereof.

Clause 7. The method of clause 1, wherein a combination of oxysterols is administered.

Clause 8. The method of clause 7, wherein the combination of oxysterols is 20α-hydroxycholesterol, 24(R)-hydroxycholesterol, and 24(S)-hydroxycholesterol; or pharmaceutically acceptable salts thereof.

Clause 9. The method of clause 1, wherein the disease or disorder is selected from at least one of necrotizing enterocolitis, mesenteric ischemia, inflammatory bowel diseases including Crohn's disease and ulcerative colitis, lymphocytic colitis, Celiac disease, Behcet's disease, rheumatoid arthritis, psoriasis, and autoimmune thyroid disease.

Clause 10. The method of clause 1, wherein the oxysterol reduces inflammation.

Clause 11. The method of clause 1, wherein the oxysterol is administered in combination, simultaneously or sequentially, with an additional therapeutic agent.

Clause 12. The method of clause 11, wherein the additional therapeutic agent is an antibiotic.

Clause 13. The method of clause 12, wherein the antibiotic is selected from the group consisting of ampicillin, gentamycin, zosyn, vancomycin, or a combination thereof.

Clause 14. The method of clause 12, wherein the disease is necrotizing enterocolitis.

Clause 15. The method of clause 11, wherein additional therapeutic agent is an immunosuppressive agent.

Clause 16. The method of clause 15, wherein the immunosuppressive agent is selected from the group consisting of corticosteroids, Azathioprine (Imuran), mercaptopurine, infliximab, adalimumab, and certolizumab pegol, or a combination thereof.

Clause 17. The method of clause 16, wherein the disease being treated is Crohn's disease, ulcerative colitis, lymphocytic colitis, Celiac Disease, Behcet's disease, autoimmune thyroid disease, or rheumatoid arthritis.

Clause 18. The method of clause 11, wherein the additional therapeutic agent is a corticosteroid, vitamin D, a retinoid, phototherapy, and an immunosuppressant, or a combination thereof.

Clause 19. The method of clause 18, wherein the disease is psoriasis.

Clause 20. The method of clause 18, wherein the immunosuppressant is methotrexate or cyclosporine.

Clause 21. The method of clause 1, wherein the oxysterol is combined with a pharmaceutically acceptable carrier.

Clause 22. The method of clause 21, wherein the oxysterol and pharmaceutically acceptable carrier are administered orally, intravenously, or transdermally.

Clause 23. The method of clause 1, wherein the oxysterol is administered orally, intravenously, or transdermally.

Clause 24. A pharmaceutical composition comprising at least one oxysterol and at least one pharmaceutically acceptable carrier.

Clause 25. The pharmaceutical composition of clause 16, further comprising human breast milk.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating necrotizing enterocolitis in a subject in need thereof, the method comprising administering to the subject a therapeutically effective amount of at least one oxysterol, wherein the at least one oxysterol is 20α-hydroxycholesterol, 22(R)-hydroxycholesterol, 22(S)-hydroxycholesterol, 24(R)-hydroxycholesterol, 24(S)-hydroxycholesterol, 25-hydroxycholesterol, 27-hydroxycholesterol, or a pharmaceutically acceptable salt thereof.

2. The method of claim 1, wherein the at least one oxysterol is 20α-hydroxycholesterol, 24(R)-hydroxycholesterol, 24(S)-hydroxycholesterol, or a pharmaceutically acceptable salt thereof.

3. The method of claim 1, further comprising administering a second oxysterol.

4. The method of claim 3, wherein the second oxysterol is 20α-hydroxycholesterol, 24(R)-hydroxycholesterol, 24(S)-hydroxycholesterol, or pharmaceutically acceptable salts thereof.

5. The method of claim 1, further comprising administering an additional therapeutic agent, wherein the additional therapeutic agent is administered in combination, simultaneously, or sequentially with the at least one oxysterol.

6. The method of claim 5, wherein the additional therapeutic agent is an antibiotic.

7. The method of claim 6, wherein the antibiotic is selected from the group consisting of ampicillin, gentamycin, zosyn, vancomycin, or a combination thereof.

8. The method of claim 1, wherein the at least one oxysterol is combined with a pharmaceutically acceptable carrier.

9. The method of claim 8, wherein administering the at least one oxysterol combined with the pharmaceutically acceptable carrier comprises oral, intravenous, and transdermal administration.

10. The method of claim 1, wherein the at least one oxysterol is administered orally, intravenously, or transdermally.

11. The method of claim 1, wherein the subject is a premature infant.

12. The method of claim 2, wherein the at least one oxysterol is 20α-hydroxycholesterol or a pharmaceutically acceptable salt thereof.

13. The method of claim 2, wherein the at least one oxysterol is 24(R)-hydroxycholesterol or a pharmaceutically acceptable salt thereof.

14. The method of claim 2, wherein the at least one oxysterol is 24(S)-hydroxycholesterol or a pharmaceutically acceptable salt thereof.

* * * * *